United States Patent
Jo

(10) Patent No.: US 11,542,491 B2
(45) Date of Patent: Jan. 3, 2023

(54) FUSION TAG FOR INCREASING WATER SOLUBILITY AND EXPRESSION LEVEL OF TARGET PROTEIN AND USES THEREOF

(71) Applicant: INDUSTRY-ACADEMIC COOPERATION FOUNDATION GYEONGSANG NATIONAL UNIVERSITY, Gyeongsangnam-do (KR)

(72) Inventor: Byung-hoon Jo, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

(*) Notice: Subject to any disclaimer, the term of this patent is extended or adjusted under 35 U.S.C. 154(b) by 162 days.

(21) Appl. No.: 16/772,890

(22) PCT Filed: Dec. 28, 2018

(86) PCT No.: PCT/KR2018/016853
§ 371 (c)(1),
(2) Date: Jun. 15, 2020

(87) PCT Pub. No.: WO2019/135559
PCT Pub. Date: Jul. 11, 2019

(65) Prior Publication Data
US 2021/0163914 A1   Jun. 3, 2021

(30) Foreign Application Priority Data
Jan. 3, 2018   (KR) .................. 10-2018-0000727

(51) Int. Cl.
*C12N 9/88* (2006.01)
(52) U.S. Cl.
CPC ........ *C12N 9/88* (2013.01); *C12Y 402/01001* (2013.01); *C07K 2319/00* (2013.01)
(58) Field of Classification Search
CPC .............. C12N 9/88; C12Y 402/01001; C07K 2319/00; C07K 7/06; C07K 14/195; C07K 2319/02
See application file for complete search history.

(56) References Cited

U.S. PATENT DOCUMENTS

2012/0107876 A1   5/2012   Banerjee et al.

FOREIGN PATENT DOCUMENTS

| KR | 10-2012-0006002 A | 1/2012 |
| KR | 2015122542 A * | 11/2015 |
| KR | 20150122542 A * | 11/2015 |
| KR | 10-1591786 B1 | 2/2016 |
| WO | 2017/011909 A1 | 1/2017 |

OTHER PUBLICATIONS

International Search Report for PCT/KR2018/016853 dated Apr. 8, 2019.
NCBI GenBank database accession No. KDN95606.1, "carbonate dehydratase [Hydrogenovibrio marinus]", May 29, 2014.
NCBI GenBank database accession No. ABB42137.2, "carbonic anhydrase, alpha family [Hydrogenovibrio crunogenus XCL-2]", Jan. 28, 2014.
Sofia J. Costa et al., "The novel Fh8 and H fusion partners for soluble protein expression in *Escherichia coli*: a comparison with the traditional gene fusion technology", Applied Microbiology and Biotechnology, vol. 97, (15), pp. 6779-6791, 2013.
Sofia Costa et al., "Fusion tags for protein solubility, purification and immunogenicity in *Escherichia coli*: the novel Fh8 system", Frontiers in Microbiology, vol. 5, (63), pp. 1-20, 2014.
Douglas Hanahan, "Studies on Transformation of *Escherichia coli* with plasmids", J. Mol. Biol. vol. 166, pp. 557-580, 1983.

* cited by examiner

*Primary Examiner* — Iqbal H Chowdhury
(74) *Attorney, Agent, or Firm* — The PL Law Group, PLLC

(57) ABSTRACT

A fusion tag according to an embodiment of the present invention may increase the water solubility and expression level of a target protein. As the water solubility and expression level of a target protein in host cell can be increased by a recombinant vector including the fusion tag, the fusion tag can be advantageously used in industry.

14 Claims, 10 Drawing Sheets
Specification includes a Sequence Listing.

FUSION TAG FOR INCREASING WATER SOLUBILITY AND EXPRESSION LEVEL OF TARGET PROTEIN AND USES THEREOF

GOVERNMENT LICENSE RIGHTS

The present invention is a result of the study which has been carried out with the support of National Research Foundation of Korea (1711056102, 20%) with funding from the Korean government (Ministry of Science and ICT, South Korea), the support of Korea Institute of Marine Science and Technology Foundation (1525006930, 30%) with funding from the Korean government (Ministry of Oceans and Fisheries, South Korea), and the support of Korea Institute of Energy Technology Evaluation and Planning (20182010600430, 50%) with funding from the Korean government (Ministry of Trade, Industry and Energy, South Korea). The government has certain rights in the invention.

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/016853 filed on Dec. 28, 2018, which claims priority to the benefit of Korean Patent Application No. 10-2018-0000727 filed in the Korean Intellectual Property Office on Jan. 3, 2018, the entire contents of which are incorporated herein by reference.

TECHNICAL FIELD

The present invention relates to a fusion tag for increasing the water solubility and expression level of a target protein and uses thereof.

BACKGROUND ART

In accordance with a development of the genetic recombination techniques, lots of useful target proteins are produced by using eukaryotes like yeast or prokaryotes like *E. coli*, and the recombinant proteins produced therefrom are widely used in bioengineering industry such as manufacturing pharmaceuticals.

In particular, due to the fast cell growth rate and relatively well-studied gene identification compared to other organisms, *E. coli* has been broadly used as a host cell for producing a target protein by genetic recombination techniques. However, when *E. coli* is used as a host cell, the yield of a protein to be produced is often low as the protein is degraded by a proteinase present in *E. coli*, and this tendency is known to be particularly strong when a polypeptide with small size like molecular weight of 10 kDa or less is to be expressed. Once the recombinant protein is overexpressed in *E. coli*, it may be accumulated, in form of an insoluble aggregate, in cytoplasm. To convert the insoluble protein into active form, it is necessary to dissolve the aggregate by using a denaturant such as urea or guanidine hydrochloride at high concentration to have a denatured structure followed by precise refolding of the denatured protein by removing the reagent used for dissolving. However, the condition for refolding varies depending on the type of protein, and a fair amount of time and money is required for figuring out the condition for efficient refolding, and there is also a case in which the refolding itself is impossible to achieve.

The most effective way of producing a recombinant protein is to produce a protein in highly soluble form while it is overexpressed in a higher amount than the detection limit. To enhance the expression efficiency of a recombinant protein, various engineerings have been made at the level of vector, host, and ORF (open reading frame). A vector is composed of factors for transcription, translation, replication, or the like and each of those factors has many variants. In recent years, new regulation factors other than those typical factors are found and an attempt is made to have their various combinations for achieving enhanced expression efficiency. By using a vector provided with a functional tag for assisting the folding or recovery of a protein during the process, the solubility of a protein may be increased or the easiness of a purification process can be improved. Because the use of a tag is not only the most universal and simple method but also a method that can guarantee the non-interference exhibiting little influence on the function of a recombinant protein, it is employed frequently.

Meanwhile, in Korean Patent Registration No. 1591786, "Composition for carbon dioxide capture comprising marine bacterium-derived recombinant biocatalyst, method for preparing the same, and method of carbon dioxde capture using the same" is disclosed, and, in Korean Patent Application Publication No. 2012-0006002. "Method for producing soluble recombinant protein by using dihydrofolate reductase as fusion expression partner" is disclosed. However, so far there is no disclosure of a fusion tag for increasing the water solubility and expression level of a target protein and uses thereof as described in the present invention.

SUMMARY

The present invention is devised under the circumstances described above. Specifically, as a result of preparing a recombinant vector in which a polynucleotide encoding a fusion tag including $PLX_1DLGX_2E$ domain that is present at the N-terminus of α-carbonic anhydrase derived from *Hydrogenovibrio marinus*, H. crunogenus, or *H. kuenenii*; or a fusion tag (trncNEXT) including part of the C-terminus of the NEXT fusion tag, and a gene encoding a target protein are operably linked to each other, and overexpressing the target protein by transforming an *E. coli* strain with the recombinant vector, it is found that the increased water solubility and increased expression level of a target protein are obtained with the fusion tag of the present invention compared to MBP (maltose binding protein), GST (glutathione S-transferase), and Fhb tag which have been conventionally used, and it is particularly found that the target protein to which a tag is fused has excellent thermal stability and, when trncNEXT tag including part of the C-terminus of NEXT tag is used, the stability of a target protein can be maintained at a similar level to NEXT tag, and the present invention is completed accordingly.

To achieve the purpose described above, the present invention provides a recombinant vector in which a polynucleotide encoding a fusion tag including $PLX_1DLGX_2E$ domain ($X_1$ is I or L and $X_2$ is A or S) composed of the amino acid sequence of SEQ ID NO: 1 or a peptide composed of the amino acid sequence of SEQ ID NO: 20 and a gene encoding a target protein are sequentially linked to each other.

The present invention further provides a host cell transformed with the recombinant vector.

The present invention further provides a method for increasing the water solubility and expression level of a target protein including transforming a host cell with the recombinant vector to express a gene encoding a target protein.

The present invention further provides a method for producing a target protein with increased water solubility and increased expression level in a host cell including: transforming a host cell with the recombinant vector; and culturing the transformed host cell to express a target protein.

The present invention still further provides a composition for producing a target protein with increased water solubility and increased expression level comprising, as an effective component, a recombinant vector in which a polynucleotide encoding a fusion tag including $PLX_1DLGX_2E$ domain ($X_1$ is I or L and $X_2$ is A or S) composed of the amino acid sequence of SEQ ID NO: 1 or a peptide composed of the amino acid sequence of SEQ ID NO: 20 and a gene encoding a target protein are sequentially linked to each other.

With a fusion tag of the present invention, the water solubility and expression level of a target protein, which is fused to the C-terminus of a fusion protein, in host cell can be increased while the functional property of a target protein is hardly affected as the fusion tag has a smaller size than MBP and Fh8 tags that are conventionally used, and thus the fusion tag of the present invention has excellent applicability. Accordingly, the fusion tag of the present invention can be utilized as a basic constitutional element of a vector system that is used for expressing a recombinant protein for pharmaceutical use, industrial use, or academic study.

BRIEF DESCRIPTION OF THE DRAWINGS

Figure 1B:
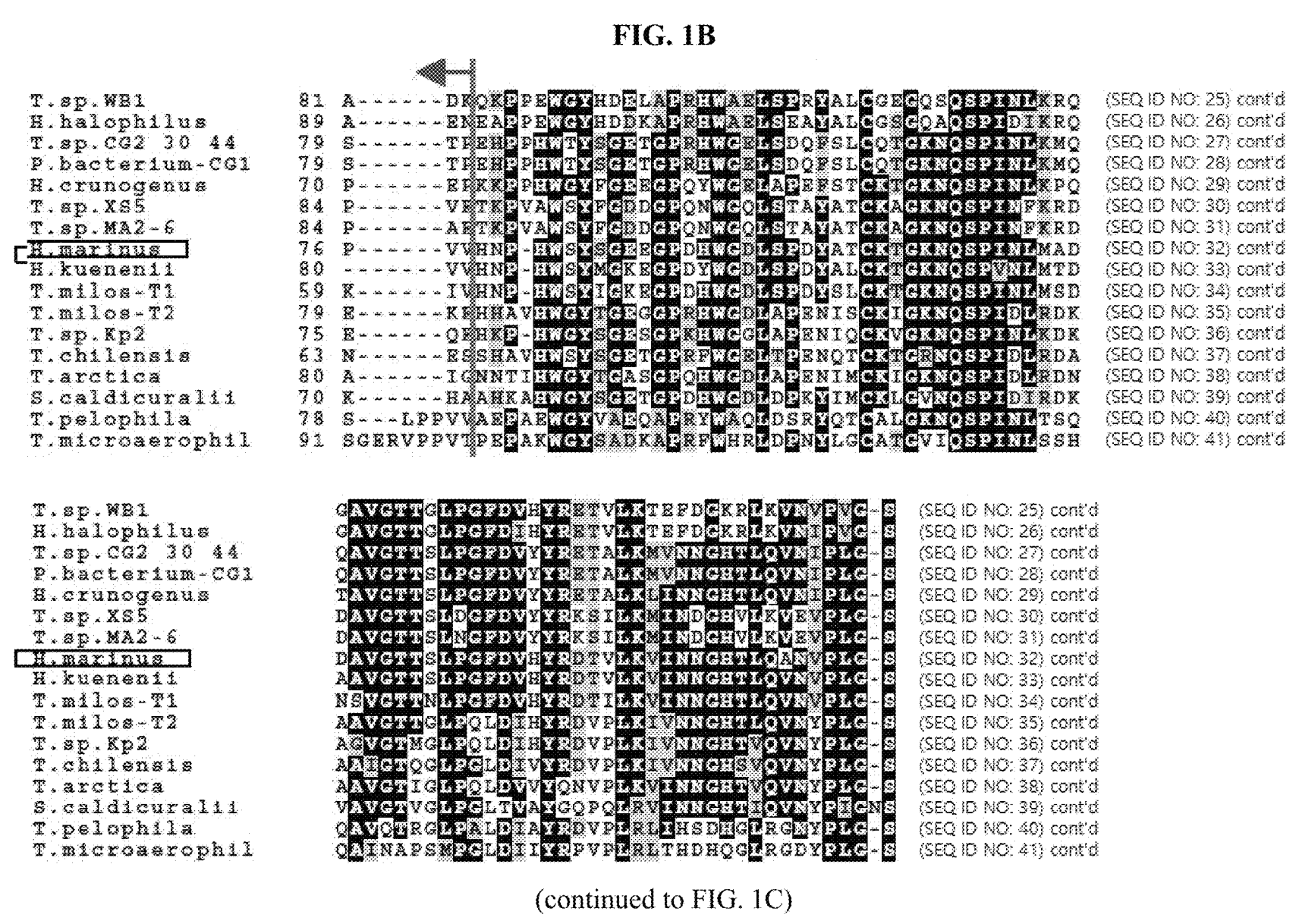
Figure 1C:
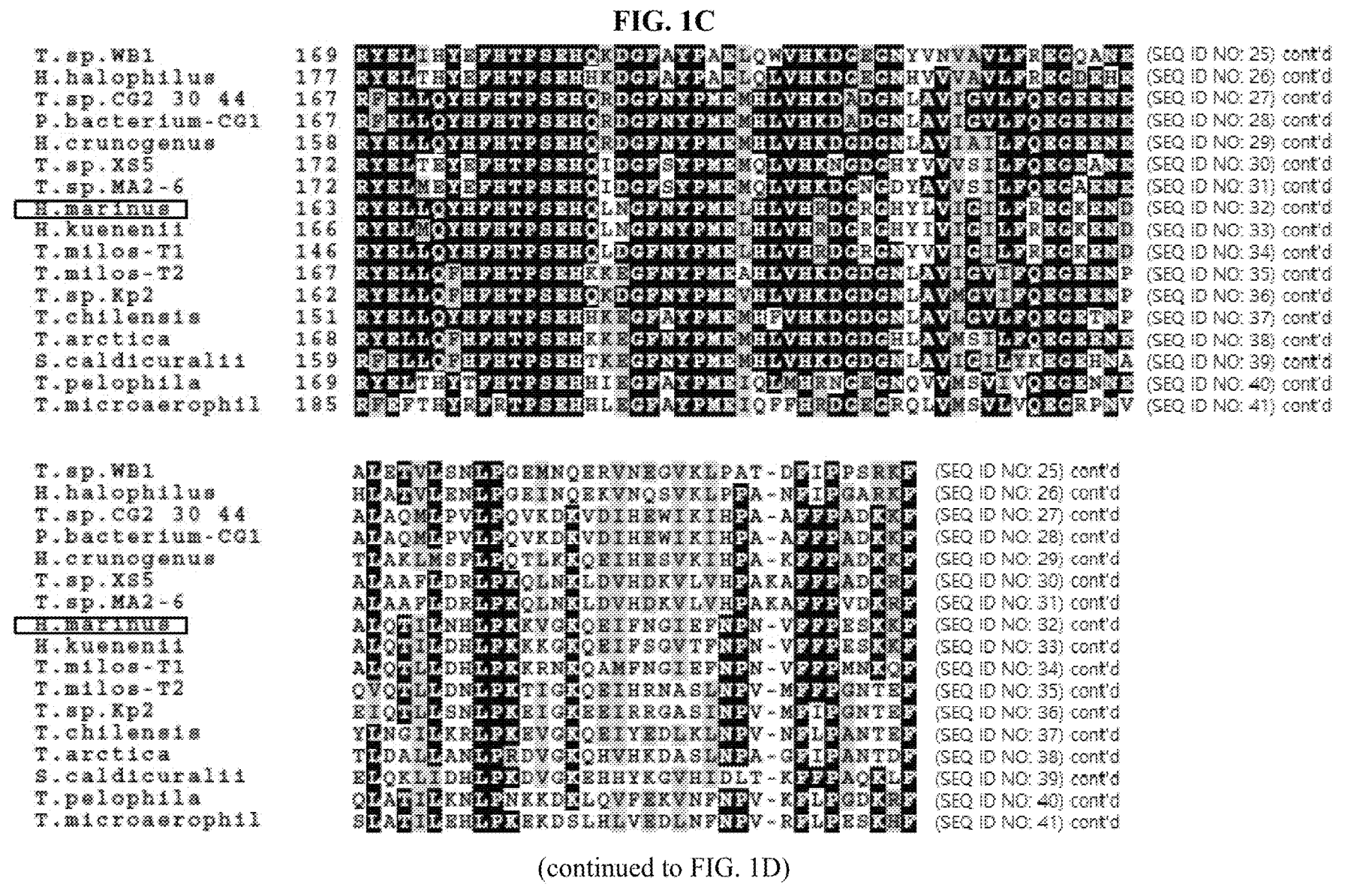

FIGS. 1A to 1D show the result of multi-alignment of the amino acid sequence of α-carbonic anhydrase which is derived from bacteria belonging to *Hydrogenovibrio* sp., *Thiomicrospira* sp., Thiomicrorhabdus sp., *Sulfurivirga* sp., or Piscirickettsiaceae sp.

DETAILED DESCRIPTION

Figure 1A:
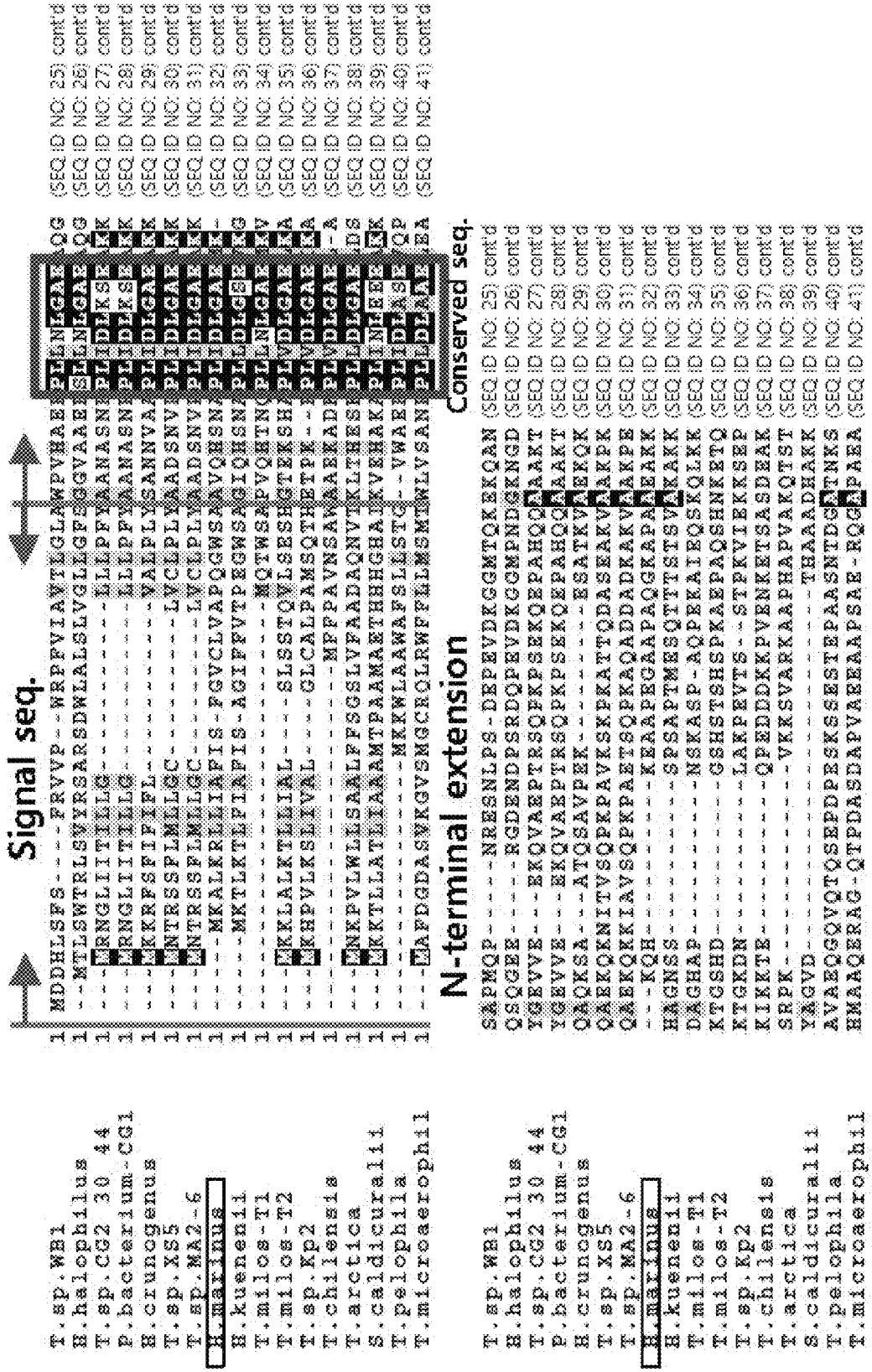
Figure 1D:
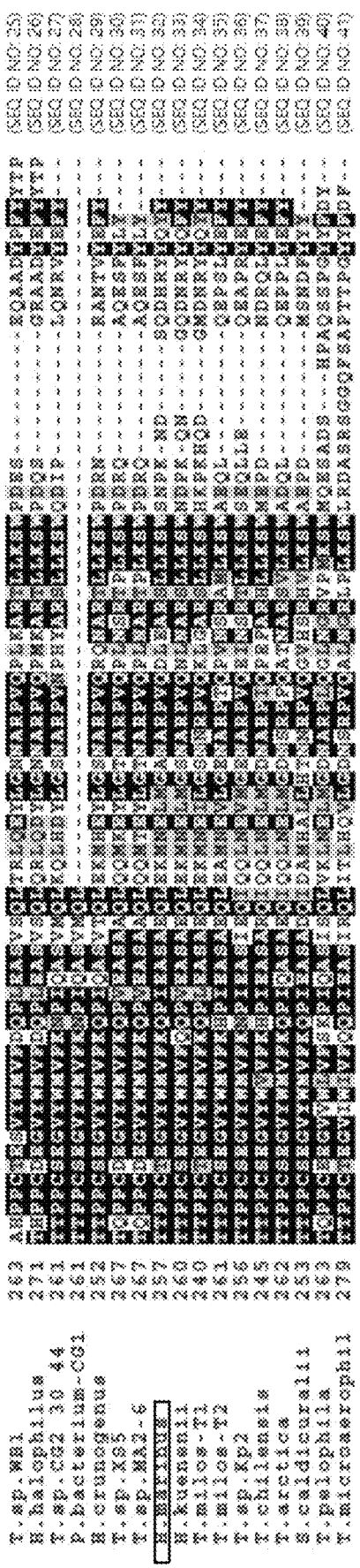

In order to achieve the purpose of the invention described above, the present invention provides a recombinant vector characterized in that a polynucleotide encoding a fusion tag including $PLX_1DLGX_2E$ domain ($X_1$ is I or L and $X_2$ is A or S) composed of the amino acid sequence of SEQ ID NO: 1 or a peptide composed of the amino acid sequence of SEQ ID NO: 20, and a gene encoding a target protein are sequentially linked to each other.

The recombinant vector according to the present invention may be a recombinant vector in which a polynucleotide encoding a fusion tag including $PLX_1DLGX_2E$ domain composed of the amino acid sequence of SEQ ID NO: 1 or a peptide composed of the amino acid sequence of SEQ ID NO: 20 and a gene encoding a target protein are operably linked to each other. As described herein, the expression "operably linked" means a component of an expression cassette which functions as a unit for expressing an exogenous protein. For example, a promoter operably linked to an exogenous DNA encoding a protein promotes the production of a functional mRNA corresponding to the exogenous DNA. As for the method of linking the promoter to a gene encoding the target protein, a common technique like PCR, digestion using restriction enzyme, and ligation, which can be easily carried out by a person skilled in the art, can be used.

With regard to the recombinant vector of the present invention, $PLX_1DLGX_2E$ domain composed of the amino acid sequence of SEQ ID NO: 1 may be a conserved sequence which is present in the N-terminus of α-carbonic anhydrase derived from microorganism. The microorganism may be a microorganism like bacteria of *Hydrogenovibrio* genus, *Thiomicrospira* genus, Thiomicrorhabdus genus, *Sulfurivirga* genus, or Piscirickettsiaceae family. It may be preferably *Hydrogenovibrio marinus, Hydrogenovibrio crunogenus, Hydrogenovibrio kuenenii, Hydrogenovibrio halophilus, Thiomicrospira* milos T1, *Thiomicrospira* milos T2, *Thiomicrospira pelophila, Thiomicrospira microaerophila, Thiomicrospira* genus Kp2, *Thiomicrospira* genus CG2_30_44_34, *Thiomicrospira* genus XS5, *Thiomicrospira* genus MA2-6, *Thiomicrospira* genus WB1, Thiomicrorhabdus *chilensis, Thiomicrorhabdus arctica, Sulfurivirga caldicuralii*) or Piscirickettsiaceae bacterium CG18_big_fil_WC_8_21_14_2_50_44_103, and it is more preferably *Hydrogenovibrio marinus, Hydrogenovibrio crunogenus* or *Hydrogenovibrio kuenenii*, but it is not limited thereto.

Although the N-terminus sequence of α-carbonic anhydrase has low sequence identity or sequence similarity among the above microorganisms and has different sequence length, the domain composed of the amino acid sequence of SEQ ID NO: 1 is included therein as a conserved sequence.

With regard to the recombinant vector of the present invention, the fusion tag including $PLX_1DLGX_2E$ domain of SEQ ID NO: 1 can be a tag including $PLX_1DLGX_2E$ domain that is present at the N-terminus of α-carbonic anhydrase derived from *Hydrogenovibrio marinus* (hereinbelow, referred to as NEXT tag), a tag including $PLX_1DLGX_2E$ domain that is present at the N-terminus of α-carbonic anhydrase derived from *Hydrogenovibrio crunogenus* (hereinbelow, referred to as Cm tag), or a tag including $PLX_1DLGX_2E$ domain that is present at the N-terminus of α-carbonic anhydrase derived from *Hydrogenovibrio kuenenii* (hereinbelow, referred to as Kue tag), and NEXT tag, Cru tag, and Kue tag can be composed of the amino acid sequence of SEQ ID NOs: 2, 3 and 4, respectively, but not limited thereto.

In addition, with regard to the recombinant vector of the present invention, a fusion tag including a peptide composed of the amino acid sequence of SEQ ID NO: 20 means a tag which is composed of the 17 amino acids that are present at the C-terminus of NEXT tag.

Also included in the scope of the fusion tag of the present invention are the tag having an amino acid sequence represented by SEQ ID NO: 2, 3 or 4, and functional equivalents thereof. As described herein, the term "functional equivalents" means a tag which has, as a result of addition, substitution, or deletion of an amino acid, at least 70%, preferably at least 80%, more preferably at least 90%, and even more preferably at least 95% sequence homology with the amino acid sequence represented by SEQ ID NO: 2, 3 or 4, and it indicates a tag which exhibits substantially the same physiological activity as the tag represented by SEQ ID NO: 2, 3 or 4. The expression "substantially the same physiological activity" indicates an activity of increasing the water solubility and expression level of a target protein.

In one embodiment of the present invention, the fusion tag composed of the amino acid sequence of SEQ ID NO: 2 or SEQ ID NO: 3 indicates the $PLX_1DLGX_2E$ domain in which $X_1$ is isoleucine (I) and $X_2$ is alanine (A), and the fusion tag composed of the amino acid sequence of SEQ ID NO: 4 indicates the $PLX_1DLGX_2E$ domain in which $X_1$ is leucine (L) and $X_2$ is serine (S).

Furthermore, the polynucleotide encoding the fusion tag composed of the amino acid sequence of SEQ ID NO: 2, 3 or 4 may be composed of the nucleotide sequence of SEQ ID NO: 5, 6 or 7, but it is not limited thereto.

As described herein, the term "target protein" indicates a protein that is desired to be produced in large amount by a skilled person in the art, and it means any protein that can be expressed in a transformant as a result of inserting a polynucleotide encoding the target protein to a recombinant expression vector. With regard to the recombinant vector of the present invention, the target protein can be a difficult-to-express protein which is hardly in water soluble form in a host cell. Although not limited thereto, it may be a protein such as toxin, antigen, antibody, or enzyme.

As described herein, the term "recombinant" indicates a cell which replicates an exogenous nucleotide or expresses the nucleotide, or a cell which expresses a peptide, an exogenous peptide, or a protein encoded by an exogenous nucleotide. Recombinant cell can express a gene or a gene fragment which is not found in natural-state cell in the form of a sense or antisense. In addition, the recombinant cell can express a gene that is found in natural state, provided that said gene is modified and re-introduced into the cell by an artificial means.

According to the present invention, the polynucleotide encoding the fusion tag and the gene sequence encoding a target protein can be inserted to the recombinant expression vector. The expression "recombinant expression vector" means a bacteria plasmid, a phage, a yeast plasmid, a plant cell virus, a mammalian cell virus, or other vector. In general, as long as it can be replicated and stabilized in a host, any plasmid or vector can be used. Important characteristic of the expression vector is that it has a replication origin, a promoter, a marker gene, and a translation control element.

The expression vector including the polynucleotide encoding a fusion tag, the gene sequence encoding a target protein, and a suitable signal for regulating transcription/translation can be constructed by a method which is well known to a person skilled in the art. Examples of such method include an in vitro recombination DNA technique, a DNA synthesis technique, and an in vivo recombination technique. The DNA sequence can be effectively linked to a suitable promoter in the expression vector in order to induce synthesis of mRNA. Furthermore, the expression vector may contain, as a site for translation initiation, a ribosome binding site and a transcription terminator.

The present invention further provides a host cell transformed with the recombinant vector.

As a host cell allowing stable and continuous cloning and expression of the vector of the present invention in a prokaryotic cell, any host cell well known in the pertinent art can be used, and examples thereof include *E. coli* BL21, *E. coli* JM109, *E. coli* RR1, *E. coli* LE392, *E. coli* B, *E. coli* X 1776, *E. coli* W3110, a strain of *Bacillus* genus such as *Bacillus subtilis* or *Bacillus thuringiensis*, and enterobacetria and bacterial strains such as *Salmonella typhimurium, Serratia marcescens*, and various *Pseudomonas*.

Furthermore, in case of transforming an eukaryotic cell with the vector of the present invention, yeast (e.g., Saccharomyce *cerevisiae; Pichia pastoris; Kluyveromyces lactis; Kluyveromyces marxianus; Yarrowia lipolytica; Hansenula polymorpha*, or the like), an insect cell (e.g., *Spodoptera frugiperda* Sf9, Sf21, High Five™), an animal cell (e.g., CHO (Chinese hamster ovary) cell line, W138, BHK, COS-7, 293, HepG2, 3T3, RIN and MDCK cell line), a plant cell, or the like can be used.

The host cell transformed with the recombinant vector according to one embodiment of the present invention can be *E. coli* BL21 (DE3), but it is not limited thereto.

When the host cell is a prokaryotic cell, the method of delivering the vector of the present invention to a host cell can be carried out by $CaCl_2$ method, Hanahan's method (Hanahan, D., 1983 J. Mol. Biol. 166, 557-580), electroporation, or the like. When the host cell is an eukaryotic cell, the vector can be incorporated to a host cell by microinjection, calcium phosphate precipitation, electroporation, liposome-mediated transfection, DEAE-dextran treatment, gene bombardment, or the like.

The present invention further provides a method for increasing the water solubility and expression level of a target protein including transforming a host cell with the recombinant vector to express a gene encoding a target protein.

In the method according to one embodiment of the present invention, the host cell can be *E. coli* BL21 (DE3), but it is not limited thereto.

The present invention further provides a method for producing a target protein with increased water solubility and increased expression level in a host cell including:

transforming a host cell with the aforementioned recombinant vector; and culturing the transformed host cell to express a target protein.

With regard to the method of producing a target protein of the present invention, culturing the transformed host cell can be carried out, by using a known technique, on a medium suitable for the production of a target protein. The suitable culture medium can be either commercially obtained or prepared based on the components and compositional ratio that are described in publications like the catalogue of American Type Culture Collection, but it is not limited thereto.

The method for producing a target protein of the present invention may also include a step of isolating and purifying the target protein from a host cell expressing the target protein. As for the method for isolation, isolation from a medium can be achieved by a common method such as centrifuge, filtration, extraction, spray drying, evaporation, or precipitation, but the method is not limited thereto. Furthermore, the isolated protein can be purified by various well-known methods such as chromatography (e.g., ion exchange, affinity, hydrophobic, or size exclusion chromatography), dialysis, electrophoresis, fractional dissolution (e.g., ammonium sulfate precipitation), SDS-PAGE, or extraction.

The present invention still further provides a composition for producing a target protein with increased water solubility and increased expression level comprising, as an effective component, a recombinant vector in which a polynucleotide encoding a fusion tag including $PLX_1DLGX_2E$ domain ($X_1$ is I or L and $X_2$ is A or S) composed of the amino acid sequence of SEQ ID NO: 1 or a peptide composed of the amino acid sequence of SEQ ID NO: 20 and a gene encoding a target protein are sequentially linked to each other. As the composition of the present invention comprises, as an effective component, a polynucleotide encoding the fusion tag that can increase the water solubility and expression level of a target protein for fusion, a target protein with increased water solubility and increased expression level can be produced.

With regard to the composition of the present invention, the fusion tag can be a tag composed of the amino acid sequence of SEQ ID NO: 2, 3 or 4, but it is not limited thereto.

Hereinbelow, the present invention is explained in detail in view of the Examples. However, it is evident that the following Examples are given only for exemplification of the present invention and by no means the present invention is limited to the following Examples.

Materials and Methods

1. Culture of Bacterial Strain

For constructing a gene recombinant vector, *E. coli* TOP10 strain was used. For protein expression, *E. coli* BL21 (DE3) strain was used. *E. coli* was cultured in Luria-Bertani (LB) medium at conditions of 37° C., 180 rpm, and 50 µg/mL ampicillin was added thereto as required.

2. Cloning of Water Soluble Tag for Constructing Plasmid Vector

For cloning a fusion tag from the α-carbonic anhydrase derived from *Hydrogenovibrio marinus* DSM 11271 strain (hereinbelow, NEXT), DNA fragments amplified by PCR, in which the genomic DNA of H marinus has been used as a template, were obtained. Similarly, by using as a template pMAL-c5X for MBP (maltose-binding protein) tag and pGEX-4T-1 for GST (glutathione S-transferase) tag, PCR was carried out to obtain DNA fragments. The primer sequences used for PCR are as described in the following Table 1.

Furthermore, for the fusion tag derived from H. crunogenus and *H. kuenenii* strains, respectively (hereinbelow, Cru, Kue), and Fhb tag, gene synthesis was carried out such that each tag contains its whole sequence (Genbank accession number: CP000109, WP_024851558, AF213970), a restriction enzyme sequence required for cloning, and GS linker sequence. All of the tags were designed such that they have NdeI restriction enzyme site in 5' area and NcoI restriction enzyme site in 3' area and also a flexible GS linker (GGGGSGGGGS (SEQ ID NO: 24)) is additionally added between the tag and a target protein.

The PCR amplified product was cloned in pGEM-T easy vector. After sequencing, it was cloned in the expression vector pET-22b(+) using the sequences of the restriction enzyme NdeI and NcoI. The complete vector was named pET-NEXT, pET-Cru, pET-Kue, pET-MBP, pET-GST, and pET-Fh8, respectively.

Table 1

TABLE 1

Primer Sequence Information

| Primer Name | Nucleotide Sequence (5'→3') (SEQ ID NO:) |
|---|---|
| NEXT tag_F | CATATGGCTGTTCAACATAGCAATGCCCC (SEQ ID NO: 8) |
| NEXT tag_R | CCATGGAGCCTCCACCGCCGCTGCCACCT CCGCCCACAACGGGTTTTGGTTTAG (SEQ ID NO: 9) |
| MBP tag_F | CATATGAAAATCGAAGAAGGTAAACTG (SEQ ID NO: 10) |
| MBP tag_R | CCATGGAGCCTCCACCGCCGCTGCCACCT CCGCCAGTCTGCGCGTCTTTC (SEQ ID NO: 11) |
| GST tag_F | CATATGTCCCCTATACTAGGTTATTGG (SEQ ID NO: 12) |

TABLE 1-continued

Primer Sequence Information

| Primer Name | Nucleotide Sequence (5'→3') (SEQ ID NO:) |
|---|---|
| GST tag_R | CCATGGAGCCTCCACCGCCGCTGCCACCT CCGCCATCCGATTTTGGAGGATGG (SEQ ID NO: 13) |

3. Cloning of Target Protein for Constructing Plasmid Vector

In order to determine whether or not NEXT, Cru and Kue fusion tags of the present invention increase, as a fusion partner, the water solubility and expression level of a target protein, green fluorescent protein (GFP) and firefly luciferase, which show low water solubility after expression of a recombinant protein, and α-carbonic anhydrase derived from *Thermovibrio ammonificans* (taCA), which is expressed as a protein in water soluble form but shows low water solubility due to precipitation after protein purification, were selected as a target protein. Their genes were obtained by carrying out PCR by using pTrcHis-GFPuv, pGL-4-50, and pET-taCA, respectively, as a template.

PCR-amplified product was first cloned in pGEM-T Easy vector. After sequencing, it was cloned, by using the restriction enzyme NcoI-XhoI sequence, in pET-NEXT, pET-Cru, pET-Kue, pET-MBP, pET-GST, or pET-Fh8 vector which have been constructed as described in the above. Based on this process, 14 kinds of a plasmid for expressing total 14 kinds of proteins (NEXT tag-GFP, NEXT tag-luciferase, NEXT tag-taCA, Cru tag-taCA, Kue tag-taCA, MBP tag-GFP, MBP tag-luciferase, MBP tag-taCA, GST tag-GFP, GST tag-luciferase, GST tag-taCA, Fh8 tag-GFP, Fh8 tag-luciferase, Fh8 tag-taCA) were prepared. At the C-terminus of 14 kinds of the obtained recombinant protein, a histidine tag provided by pET-22b was fused for expression.

Furthermore, to construct an expression vector for taCA protein by using tmcNEXT fusion tag which is composed of 17 amino acid of the C-terminus of NEXT tag, tmcNEXT_F and taCA_R primers were used, and PCR was carried out by using a plasmid for expressing NEXT tag-taCA as a template. After that, by utilizing the restriction enzyme NcoI-XhoI sequence, it was cloned in pET-22b vector. In the complete vector, tmcNEXT fusion tag and taCA were fused to each other and expressed.

Meanwhile, as a β-carbonic anhydrase variant derived from *Desulfovibrio vulgaris* which is known to have excellent thermal stability, dvCA 8.0 was used as a comparison group for a test in which the stability is compared between the wild-type taCA protein not fused with NEXT tag and taCA protein fused with NEXT tag. pET-dvCA8 vector for expressing dvCA 8.0 was constructed by cloning dvCA 8.0 gene (SEQ ID NO: 22) in expression vector pET-22b by using restriction enzyme NdeI-XhoI sequence. The amino acid sequence of dvCA 8.0 was represented by SEQ ID NO: 23, and the primer sequences used for PCR are as described in the following Table 2.

Table 2

Primer Sequence Information

| Primer Name | Nucleotide Sequence (5'→3') (SEQ ID NO) |
|---|---|
| GFP_F | CCATGGGCAGTAAAGGAGAAGAACTT TTCACTG (SEQ ID NO: 14) |

Table 2-continued

Primer Sequence Information

| Primer Name | Nucleotide Sequence (5'→3') (SEQ ID NO) |
|---|---|
| GFP_R | CTCGAGTTTGTAGAGCTCATCCATGC (SEQ ID NO: 15) |
| Luciferase_F | CCATGGAAGATGCCAAAAACATTAAG (SEQ ID NO: 16) |
| Luciferase_R | CTCGAGCACGGCGATCTTGCC (SEQ ID NO: 17) |
| taCA_F | CCATGGGTGGTGGCG (SEQ ID NO: 18) |
| taCA_R | CTCGAGCTTCATCACTTTAC (SEQ ID NO: 19) |
| trncNEXT_F | CATATGGCCGCGGAAGCCAAAAA (SEQ ID NO: 21) |

4. Cell Fractionation and Protein Expression

The above-constructed recombinant vector was introduced to *E. coli* BL21 (DE3) strain and cultured at 37° C., 180 rpm. When the cell density was close to $OD_{600}$ of 0.6 to 0.8, the expression was induced by adding IPTG (isopropyl-β-D-thiogalactopyranoside) (0.01 mM at 25° C., or 1 mM at 37° C.), and cultured for 20 hours and 10 hours, respectively. Upon the completion of the culture, centrifuge was carried out for 15 minutes at condition of 4° C., 4,000×g to collect the cells, which were then resuspended by using lysis buffer (50 mM sodium phosphate, 300 mM NaCl, 10 mM imidazole, pH 8.0). The resuspended cells were disrupted in cold state by ultrasonication, and the resulting solution was centrifuged for 10 minutes at a rate of 10,000×g at 4° C. After that, the supernatant was named soluble fraction (S), and the pellet was resuspended in the same amount of lysis buffer and named insoluble fraction (IS). Each cell fraction was then separated by using SDS-PAGE (sodium dodecyl sulfate-polyacrylamide gel electrophoresis), and, according to Coomassie blue staining, the expression pattern of the recombinant protein was analyzed. Furthermore, depending on the case, the protein on gel after SDS-PAGE was transferred to a nitrocellulose membrane, and subjected to Western blot using monoclonal anti-His6 antibody as a primary antibody and polyclonal anti-mouse IgG antibody linked with alkaline phosphatase as a secondary antibody.

5. Purification of Target Protein Including Tag

From the water soluble fraction (S) containing the wild-type taCA protein not including any tag, target protein taCA including tag or dvCA 8.0, proteins were purified and their properties were analyzed. To the water soluble fraction obtained from cell culture of *E. coli* which has been transformed with the plasmid containing the wild-type taCA, dvCA8.0 or taCA containing water soluble tag (NEXT tag-taCA, Cru tag-taCA, Kue tag-taCA, MBP tag-taCA, GST tag-taCA, Fhb tag-taCA, trncNEXT tag-taCA), $Ni^{2+}$-nitrilotriacetic acid agarose beads were added and the binding reaction was allowed to occur. After that, purified proteins were obtained by using elution buffer (50 mM sodium phosphate, 300 mM NaCl, 250 mM imidazole, pH 8.0). The obtained proteins were subjected to buffer exchange using dialysis buffer (20 mM sodium phosphate buffer, pH 7.5), and, depending on the case, 300 mM sodium chloride was added to the dialysis buffer.

6. Protein Quantification

To adjust the purified protein concentration at the same level, protein quantification was carried out. Specifically, proteins obtained after the dialysis were denatured by mixing with a denaturing buffer (6 M guanidine hydrochloride GuHCl/20 mM sodium phosphate buffer, pH 7.5) and heating at 100° C. for 5 minutes, and the absorbance at 280 nm was measured. Based on the measured absorbance and the extinction coefficient at 280 nm which has been calculated from the amino acid sequence of protein, the protein concentration was determined. Calculation of the extinction coefficient was performed by using ProtParam.

7. Measurement of Enzyme Activity and Stability

Activity of the taCA protein was measured by $CO_2$ hydration assay. 600 μl of 20 mM Tris buffer (100 μM phenol red, pH 8.3) which has been kept cold was admixed with 10 μl of a protein sample. After adding the mixture to a disposable cuvette, it was placed in a spectrometer kept at 4° C. Five minutes later, 400 μl of cold $CO_2$ saturated solution were rapidly added thereto and a change in absorbance at 570 nm was measured. Time (t) for having the absorbance drop from 1.2, which is the absorbance corresponding to pH 7.5, to 0.18, which is the absorbance corresponding to pH 6.5, was obtained. In addition, by using the dialysis buffer instead of a protein sample, time required for natural $CO_2$ reaction was obtained (i.e., to: blank), and the enzyme activity was calculated using the formula $(t_0-t)/t$. To measure the stability, a sample at the same concentration was heated at 70° C. or 90° C. for a certain period of time. Then, the activity was measured and the result was compared with the activity of a sample not treated with heat. The relative activity was obtained accordingly.

8. Analysis of Predicted Phosphorylation Site

Analysis of the predicted phosphorylation site in each tag sequence was performed by using NetPhos 3.1 server.

Example 1. Analysis of Expression Pattern of Target Protein Including Water Soluble Tag 1-1. Expression of Target Protein GFP Analysis was made to see the expression of target protein GFP (NEXT tag-GFP, MBP tag-GFP, GST tag-GFP, Fh8 tag-GFP) in the cells transformed with a recombinant vector, which includes the fusion tag (NEXT) of the present invention, or MBP, GST or Fh8 tag that are conventionally used.

Figure 2:
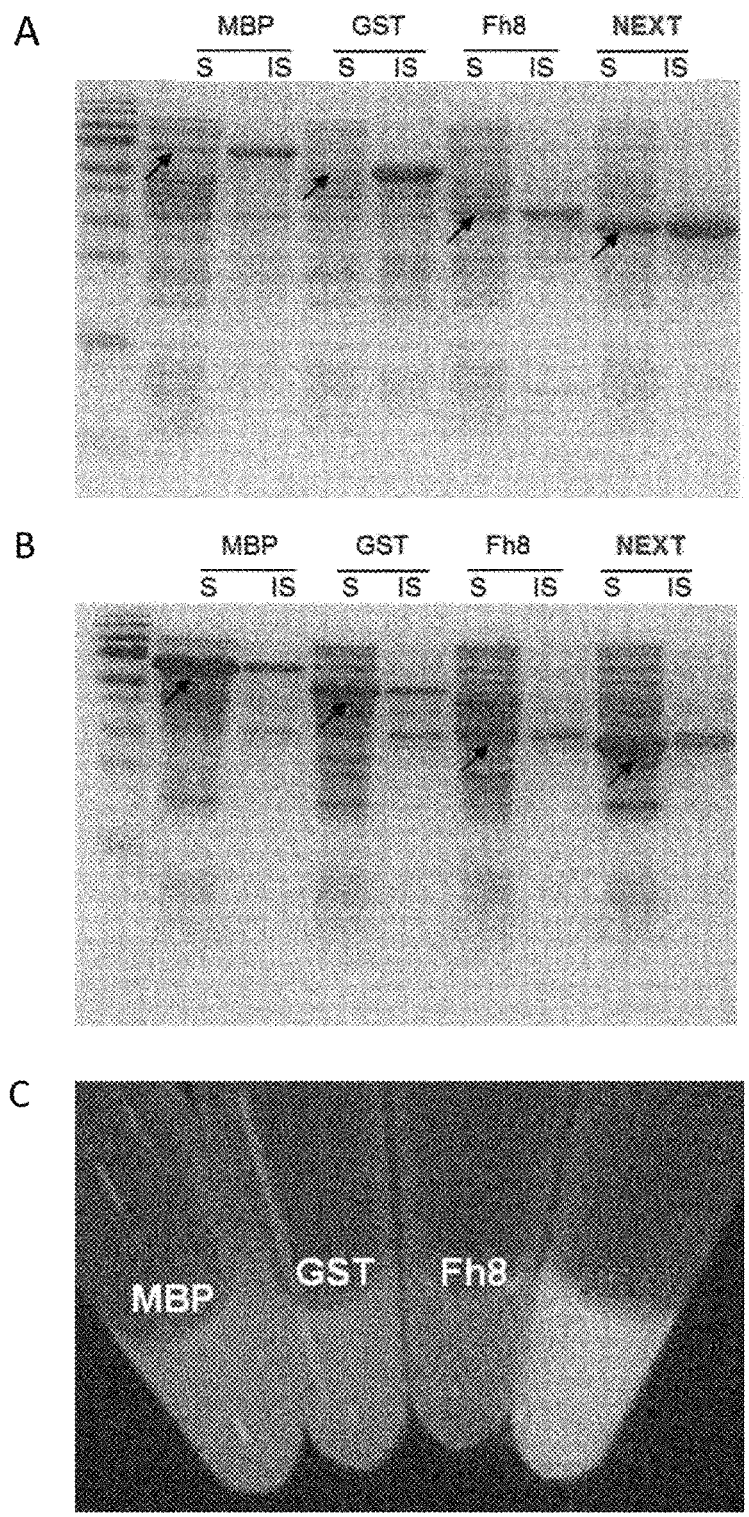
FIG. 2 shows (A, B) the photographic image of a Coomassie blue-stained gel in which the expression pattern of GFP (green fluorescent protein) fused with a different tag (i.e., NEXT, MBP, GST, or Fh8) is shown, and (C) the result of fluorescence intensity analysis. Specifically, (A); the result obtained after inducing protein expression at 37° C. by adding 1 mM IPTG to transformed cells. and (B); the result obtained after inducing protein expression at 25° C. by adding 0.01 mM IPTG to transformed cells, in which S; soluble fraction, IS; insoluble fraction, arrow; recombinant protein.

As a result, when the expression was induced at a condition including addition of 1 mM IPTG and 37° C., it was found that the target protein fused with the tag of the present invention (NEXT tag-GFP) has a higher expression amount of the recombinant protein in water soluble fraction compared to the target protein fused with other tag (i.e., MBP tag-GFP, GST tag-GFP and Fh8 tag-GFP), and also it is most excellent in terms of the total protein expression amount (A of FIG. 2). In addition, according to the result obtained by inducing the expression at 25° C. after adding 0.01 mM IPTG, all the target proteins were overexpressed in water soluble fraction regardless of the type of a tag. However, it was found that the most excellent water solubility and expression amount are obtained from the NEXT tag-GFP, to which the tag of the present invention is fused, along with MBP tag-GFP (B of FIG. 2).

Meanwhile, Coomassie blue staining is dependent on the size (kDa) and composition of a protein, and thus, based on the intensity of a protein band only, the protein expression level cannot be accurately compared. As such, analysis of the fluorescence intensity of GFP protein was carried out. As a result, it was observed that the fluorescence is the strongest from NEXT tag-GFP (C of FIG. 2). It was recognized based on this result that significantly enhanced expression of a target protein with increased water solubility can be obtained when NEXT tag of the present invention is fused to a target protein.

1-2. Expression of Target Protein Luciferase

Expression pattern of a recombinant protein fused with different tag was analyzed in the same manner as Example 1-1 except that the type of a target protein is changed.

Figure 3:
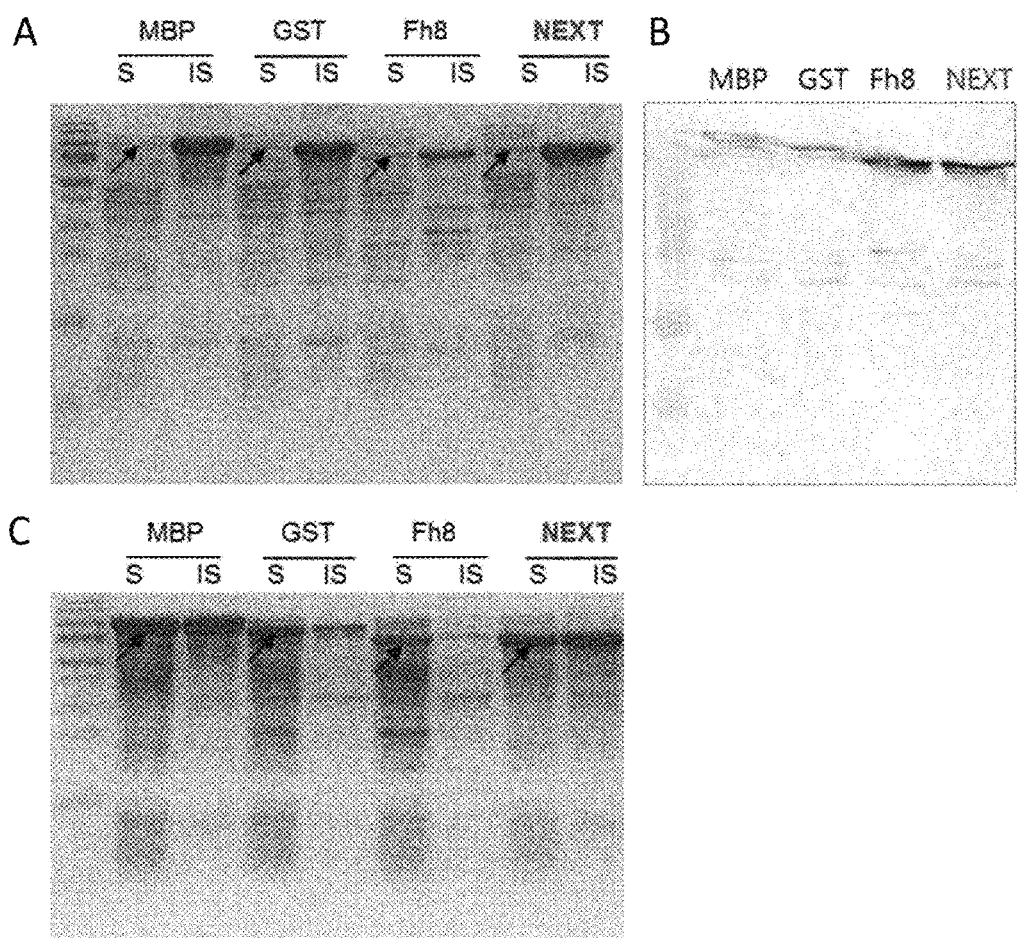
FIG. 3 shows (A, C) the photographic image of a Coomassie blue-stained gel in which the expression pattern of luciferase fused with a different tag (i.e., NEXT, MBP, GST, or Fh8) is shown, and (B) the result of Western blot. Specifically, (A); the result obtained after inducing protein expression at 37° C. by adding 1 mM IPTG to transformed cells. and (C); the result obtained after inducing protein expression at 25° C. by adding 0.01 mM IPTG to transformed cells, in which S; soluble fraction, IS; insoluble fraction, arrow; recombinant protein.

As a result, same as the result of GFP protein, it was recognized that significantly increased water solubility and expression of a recombinant luciferase protein can be obtained when NEXT tag of the present invention is fused to a target protein (FIG. 3).

1-3. Expression of Target Protein taCA

Analysis was made to see the expression of target protein taCA in the cells transformed with a recombinant vector, which includes the fusion tag (NEXT, Cru and Kue) of the present invention, or MBP, GST or Fhb tag that are conventionally used.

Figure 4:
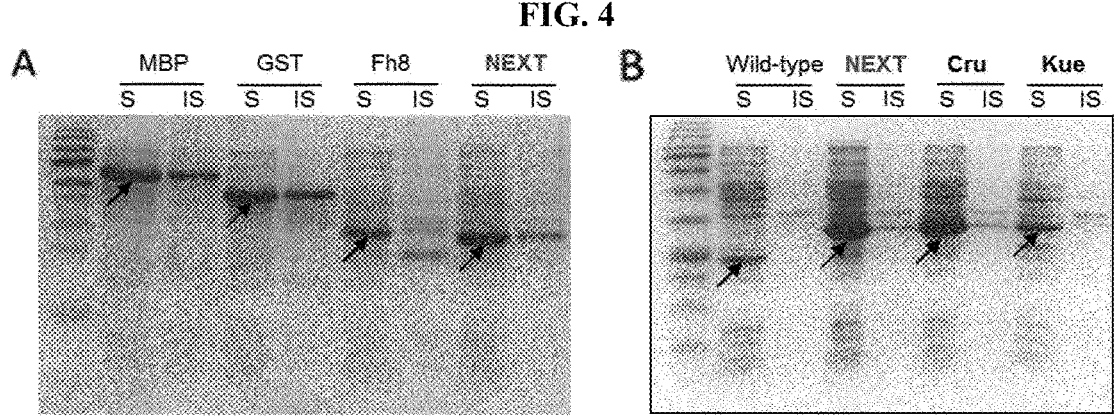
FIG. 4 shows (A) the photographic image of a Coomassie blue-stained gel to determine (A) the expression pattern of taCA (*Thermovibrio ammonificans* carbonic anhydrase) protein fused with a different tag (i.e., NEXT, MBP, GST, or Fh8), and (B) the expression pattern of the wild-type taCA protein and the target protein taCA fused with one of the three different types of a similar tag (i.e., NEXT, Cru, or Kue), in which S; soluble fraction, IS; insoluble fraction, arrow; recombinant protein.

When the expression was induced at a condition including addition of 1 mM IPTG and 37° C. followed by Coomassie blue staining, it was found that the taCA protein fused with any one of the 6 kinds of tag is overexpressed in water soluble fraction. It is particularly found that the highest expression level is shown when NEXT tag or Cru tag of the present invention is used (A and B of FIG. 4).

Example 2. Activity and Stability of Target Protein taCA Protein

It is important for a water soluble tag not only to increase the water solubility of a target protein but also to exhibit the minimum influence on the intrinsic property of a target protein. As such, the activity and stability of a target protein taCA, which has been expressed in cells transformed with the recombinant vector including the fusion tag (NEXT) of the present invention or MBP, GST or Fh8 tag that are conventionally used, were analyzed.

taCA protein itself is expressed in water soluble form. However, after undergoing a dialysis process following protein purification, insoluble precipitates are produced again in large amounts, thus showing low yield. As such, after purifying at the same condition the recombinant proteins fused with different tags, precipitation pattern of the proteins was analyzed via a dialysis process.

Figure 5:
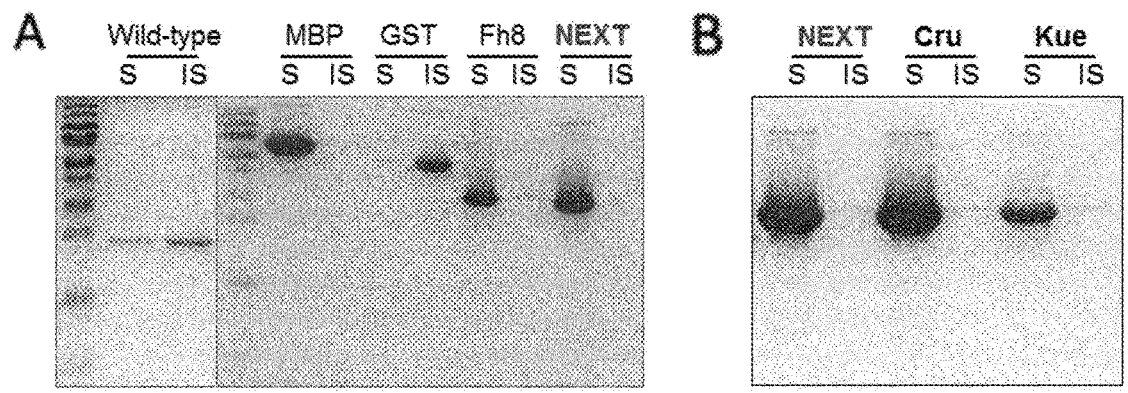
FIG. 5 shows (A) the result of analyzing precipitation pattern of the proteins which have been generated during the dialysis process after purification of the wild-type taCA protein not fused with any tag and the target protein taCA fused with a different tag (NEXT, MBP, GST, or Fh8), and (B) the result of analyzing precipitation pattern of the proteins which have been generated during the dialysis process after purification of the target protein taCA fused with one of the three different types of a similar tag (NEXT, Cru, or Kue), in which S; soluble fraction, IS; insoluble fraction, arrow; recombinant protein.

As a result, it was found that, in case of the wild-type taCA protein which has not been fused with any tag or taCA protein containing GST tag, most of the protein has precipitated in insoluble form after the dialysis process, but taCA protein containing NEXT tag, Cm tag, Kue tag, MBP tag or Fh8 tag maintained the water soluble form without being precipitated in insoluble form even after the dialysis process (A and B of FIG. 5).

Furthermore, the protein volume remained after removing the precipitates was almost the same, and, as a result of measuring the protein concentration remained after the removal of the precipitates, the concentration was found to be as follows: NEXT-taCA; 113.7 μM, MBP-taCA; 61.4 μM, GST-taCA; 2.7 μM, and Fh8-taCA; 64.2 μM. As such, it was recognized that the most excellent production amount is obtained from NEXT-taCA fused with the tag of the present invention. Based on this result, it is believed that NEXT tag of the present invention exhibits an excellent effect of increasing the water solubility of recombinant protein not only during the expression process but also during the purification process of protein.

To measure the activity of the wild-type taCA protein not fused with any tag and also the target protein NEXT-taCA, a dialysis buffer added with 300 mM sodium chloride was used. Salt was added to prevent the loss of activity of the wild-type taCA protein which is caused by precipitation occurring during the dialysis process.

Figure 6:
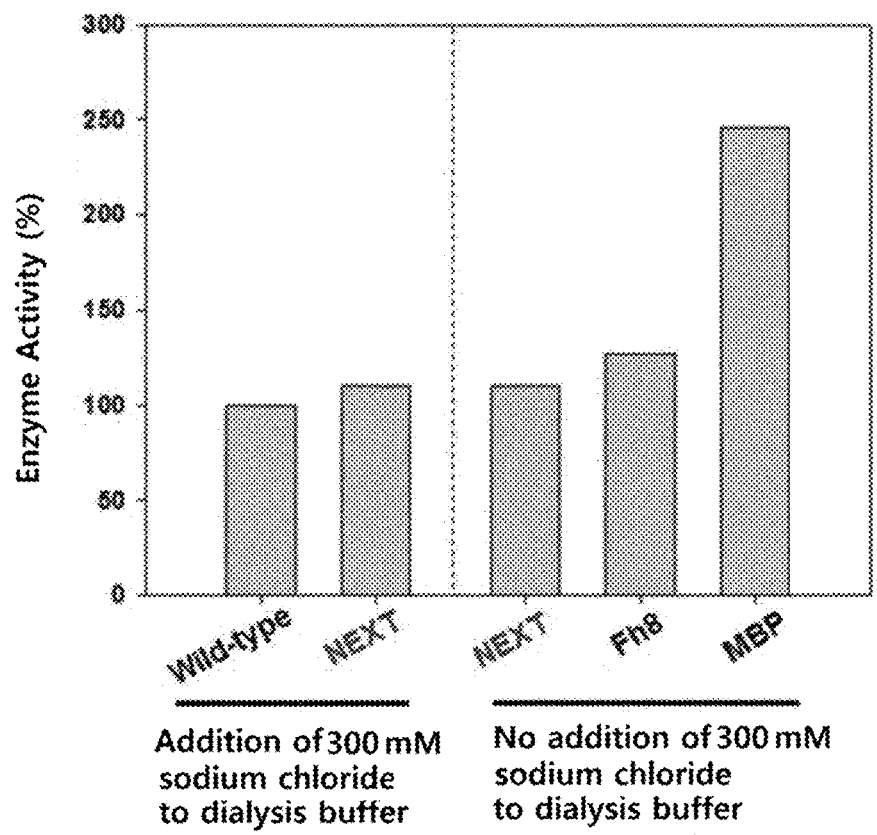
FIG. 6 shows the result of measuring the enzyme activity of the wild-type taCA protein not fused with any tag and the taCA recombinant protein fused with a different tag (NEXT, Fh8, or MBP).

As a result, it was found that the enzyme activity of target protein NEXT-taCA has increased by 10% approximately compared to the wild-type taCA protein, and the result was standardized against the measurement result of activity of target protein NEXT-taCA, Fh8-taCA and MBP-taCA, which have been obtained by using dialysis buffer not added with any sodium chloride. MBP-taCA protein showed the enzyme activity of about 250% compared to the wild-type taCA protein and Fh8-taCA protein showed the enzyme activity of about 127% compared to the wild-type taCA protein. NEXT-taCA protein showed the enzyme activity of about 110% compared to the wild-type taCA protein, representing the closest value to the original enzyme activity (FIG. 6). In case of MBP-taCA, the enzyme activity was found to be higher by 2.5 times compared to the wild-type taCA protein. However, to minimize the possibility of having an unexpected adverse effect on a target protein with various characteristics, a favorable fusion protein may be basically a fusion tag that does not exhibit any influence on the characteristics of a target protein.

Figure 7:
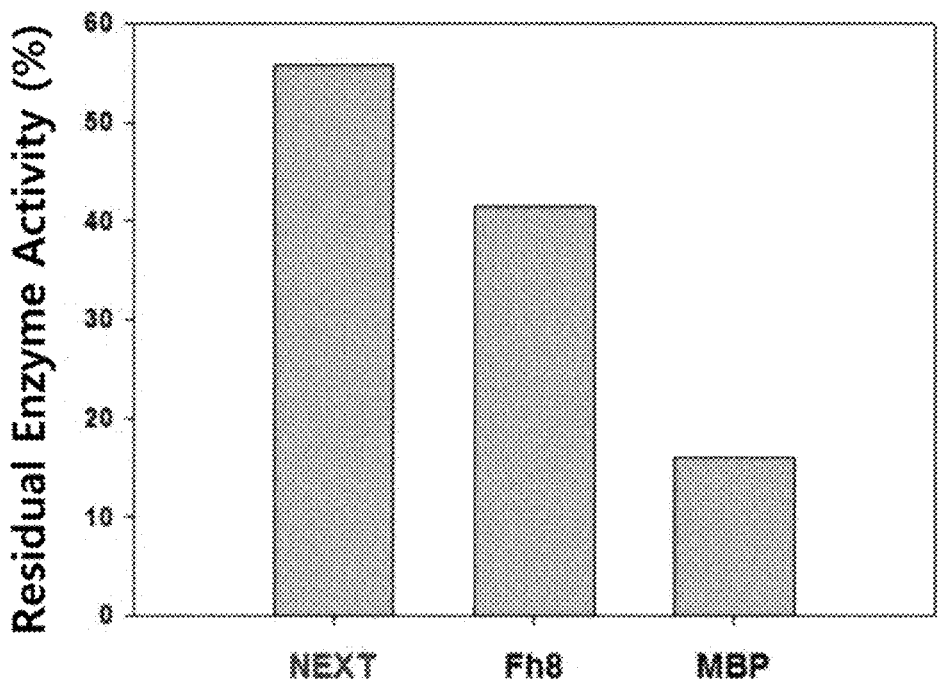
FIG. 7 shows the result of measuring the residual enzyme activity after purifying the taCA recombinant protein fused with a different tag (NEXT, Fh8, or MBP) and heating the protein for 2 hours at 90° C.

In addition, after the measurement of the enzyme activity, each recombinant protein was heated at 90° C. for 2 hours and the residual activity was measured again to analyze the thermal stability of the recombinant protein. As a result, the residual activity was about 56% for NEXT-taCA, about 41% for Fh8-taCA, and about 16% for MBP-taCA. Even though it has been shown in FIG. 5 that MBP-taCA has the highest enzyme activity, the thermal stability thereof was found to be not so high, and thus it is recognized that MBP-taCA is not suitable as a fusion tag of taCA protein. It was recognized based on these results that, when compared to other conventional tags, the intrinsic thermal stability of taCA can be maintained by use of NEXT tag of the present invention (FIG. 7).

Moreover, to determine whether or not the stability of a target protein can be maintained for an extended period of time in case of using NEXT tag, the wild-type taCA not fused with any tag, NEXT tag-taCA, and dvCA 8.0 were purified and dialyzed against the dialysis buffer which has been added with 300 mM sodium chloride. Enzyme activity was measured for each recombinant protein, which was then heated for an extended period of time at 70° C., and then the residual activity was measured again to analyze the thermal stability.

Figure 8:
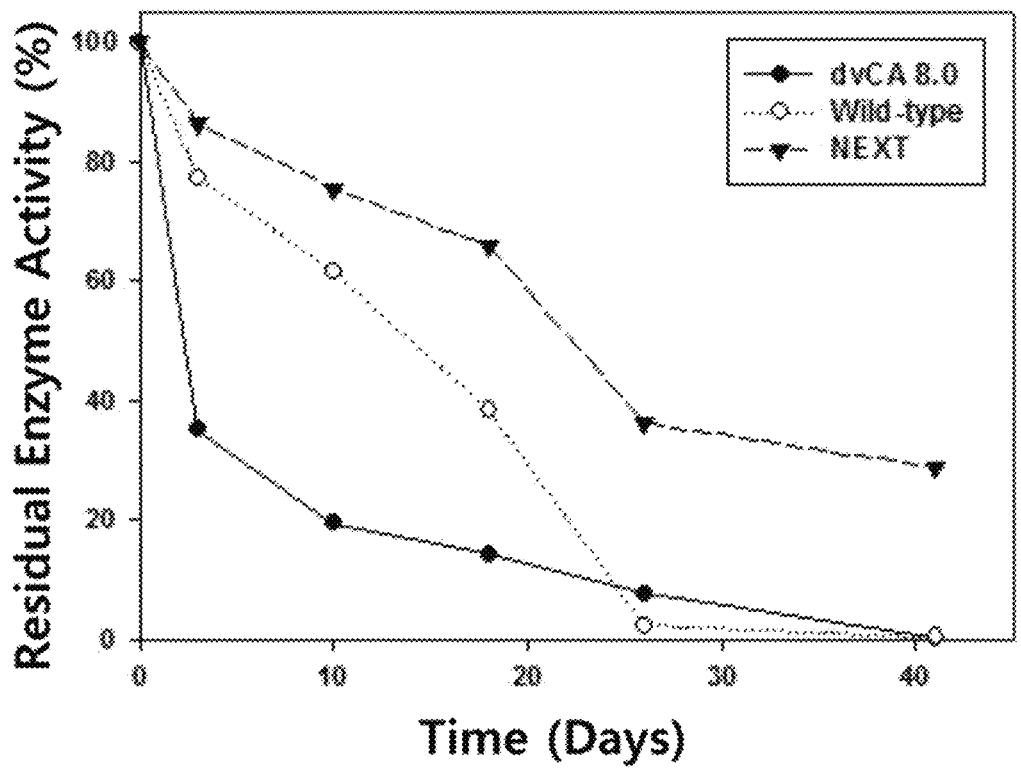
FIG. 8 shows the result of measuring the residual enzyme activity after purifying the wild-type taCA protein not fused with any tag, the taCA recombinant protein fused with NEXT tag, or the β-carbonic anhydrase variant (dvCA 8.0) derived from *Desulfovibrio vulgaris*, which is known to have excellent thermal stability, and heating the proteins at 70° C. for an extended period of time.

As a result, the residual activity of dvCA 8.0 has decreased to less than half of the initial activity within 3 days. On the other hand, the wild-type taCA and NEXT tag-taCA showed the residual activity of about 80%. After 40 days, both the wild-type taCA and dvCA 8.0 lost the entire activity, but NEXT tag-taCA exhibited the residual activity of about 30% (FIG. 8). It was recognized based on this result that, according to the fusion of NEXT tag of the present invention to a target protein, the long-term stability and enzyme usability following the stability can be further increased.

Example 3. Analysis of Phosphorylation Site in Water Soluble Tag

As shown in the following Table 3, as a result of comparing the peptide tag of the present invention (NEXT) with a water soluble tag (MBP, GST, NusA, SUMO, Fh8) that is conventionally known, it was found that NEXT tag is free of any predicted phosphorylation site.

This result means that, in NEXT tag which has a smaller size than a conventional water soluble tag, a predicted phosphorylation site possibly allowing post-translational modification like phosphorylation is absent. Furthermore, since the water soluble tags which have been conventionally used have a large size, they may exhibit an influence on the intrinsic properties of a target protein for fusion. However, as the fusion tag of the present invention (i.e., NEXT) has a relatively small size, it is believed to exhibit no influence on the functional property of a target property.

TABLE 3

Comparison of Predicted Phosphorylation Sites in Each Tag

| Tag | Size (a, a) | Predicted phosphorylation sites |
| --- | --- | --- |
| NEXT | 53 | 0 |
| MBP | 367 | 26 |
| GST | 220 | 12 |
| NusA | 495 | 33 |
| SUMO | 98 | 9 |
| Fh8 | 69 | 3 |

Example 4. Analysis of Effect of Small-Sized NEXT Tag Variant trncNEXT tag is composed of the 17 amino acids that are present at C-terminus of NEXT tag. Although it has a size of about ⅓ of NEXT tag, it was found to have the almost the same function as NEXT tag.

First, by using trncNEXT tag, the water solubility and expression level of the target protein taCA were analyzed. As a result, it was found that, although the expression level of target protein taCA to which trncNEXT is fused is slightly lower than the expression level of target protein taCA to which NEXT tag is fused, it is still expressed at higher level compared to the wild-type taCA shown in FIG. 4 (A of FIG. 9).

Figure 9:
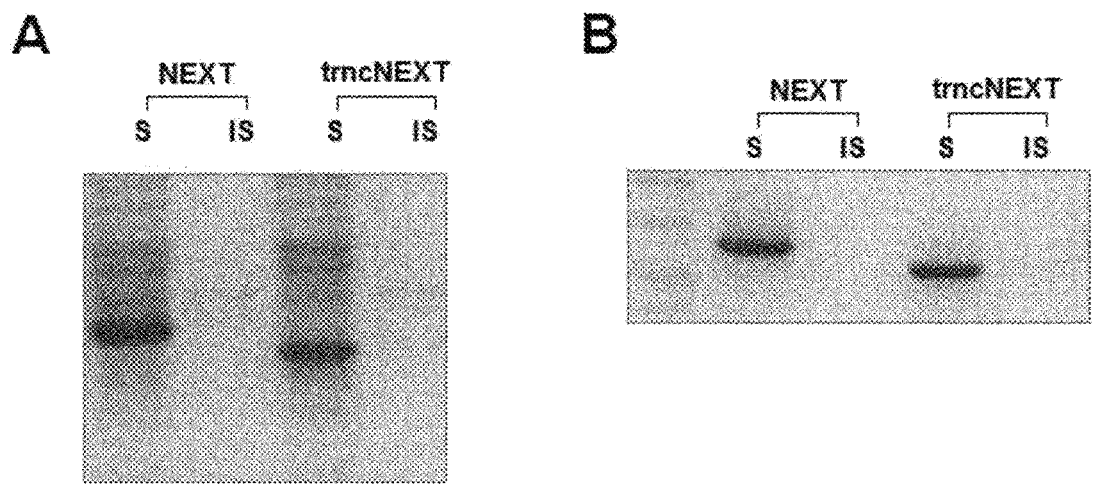
FIG. 9 shows the photographic images of a Coomassie blue-stained gel for determining (A) expression of the target protein taCA fused with NEXT tag or trncNEXT tag or (B) precipitation pattern of the protein which has been generated during dialysis after the purification, in which S; soluble fraction, IS; insoluble fraction.

Furthermore, as a result of carrying out the dialysis process using a buffer not added with sodium chloride after purifying the target proteins to which trncNEXT tag or NEXT tag is fused, it was found that trncNEXT-taCA and NEXT-taCA maintain the water soluble form without any precipitation even after the dialysis process (B of FIG. 9).

Figure 10:
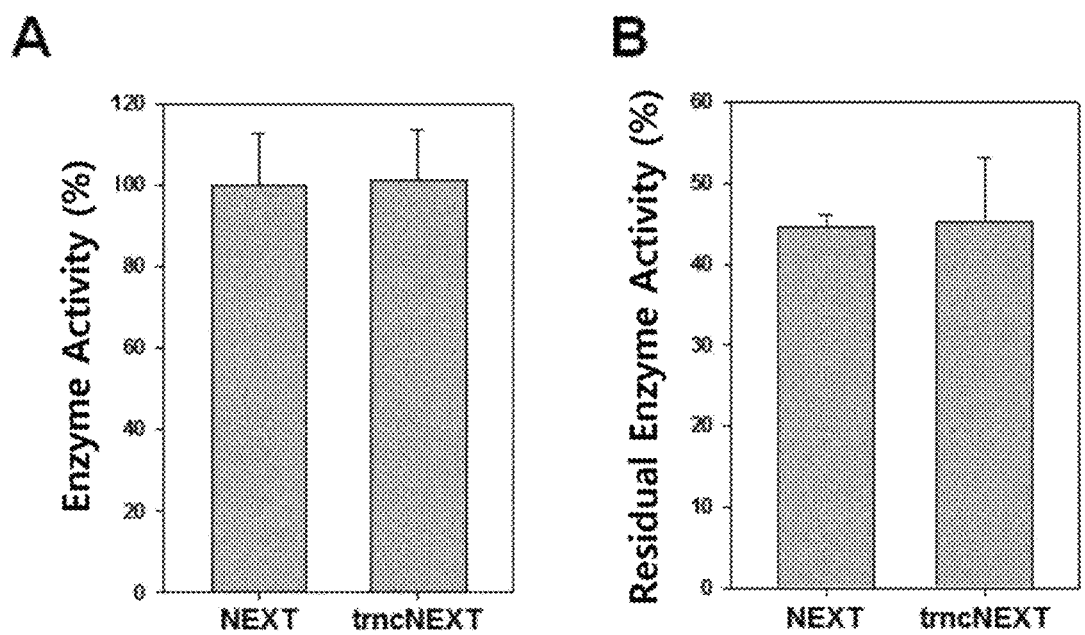
FIG. 10 shows the result of measuring (A) the relative enzyme activity of the taCA recombinant protein fused with NEXT tag or trncNEXT tag, and (B) the residual enzyme activity of the taCA recombinant protein fused with NEXT tag or trncNEXT tag after heating for 1 hour at 90° C.

Moreover, as a result of measuring the relative enzyme activity of the target protein to which trncNEXT tag or NEXT tag is fused followed by measurement of the residual activity after heating the protein for 1 hour at 90° C., it was found that, between trncNEXT-taCA and NEXT-taCA, the enzyme activity (A of FIG. 10) is almost the same as well as the residual activity after heating (B of FIG. 10).

It is recognized based on the above result that, similar to NEXT tag, trncNEXT tag can be also used as a fusion tag which is favorable in terms of increasing the water solubility and expression level of a target protein while exhibiting no influence on the intrinsic properties of a target protein.

A sequence listing electronically submitted with the present application on Jun. 15, 2020 as an ASCII text file named 20200615_Q33520GR07_TU_SEQ.TXT, created on Jun. 12, 2020 and having a size of 56,000 bytes, is incorporated herein by reference in its entirety.

What is claimed is:

1. A recombinant vector comprising:
a polynucleotide encoding a fusion tag comprising $PLX_1DLGX_2E$ domain, where $X_1$ is I or L and $X_2$ is A or S, of the amino acid sequence of SEQ ID NO: 1 or a peptide comprising the amino acid sequence of SEQ ID NO: 20; and
a gene sequentially linked to the polynucleotide, the gene encoding a target protein,
wherein the fusion tag comprises the amino acid sequence of SEQ ID NO: 2, 3 or 4.

2. The recombinant vector according to claim 1, wherein the polynucleotide encoding a fusion tag comprises the nucleotide sequence of SEQ ID NO: 5, 6 or 7.

3. The recombinant vector according to claim 1, wherein the target protein is a difficult-to-express protein.

4. A host cell transformed with the recombinant vector of claim 1.

5. A method for increasing expression level of the target protein, the method comprising transforming a host cell with the recombinant vector of claim 1 to express the gene encoding the target protein.

6. A method for producing the target protein in a host cell, the method comprising:
transforming the host cell with the recombinant vector of claim 1; and
culturing the transformed host cell to express the target protein.

7. The recombinant vector of claim 1, wherein the polynucleotide encodes the fusion tag comprising $PLX_1DLGX_2E$ domain of the amino acid sequence of SEQ ID NO: 1.

8. The recombinant vector according to claim 7, wherein the fusion tag comprises the amino acid sequence of SEQ ID NO: 2.

9. The recombinant vector according to claim 7, wherein the fusion tag comprises the amino acid sequence of SEQ ID NO: 3.

10. The recombinant vector according to claim 7, wherein the fusion tag comprises the amino acid sequence of SEQ ID NO: 4.

11. The recombinant vector according to claim 7, wherein the polynucleotide encoding the fusion tag comprises the nucleotide sequence of SEQ ID NO: 5.

12. The recombinant vector according to claim 7, wherein the polynucleotide encoding the fusion tag comprises the nucleotide sequence of SEQ ID NO: 6.

13. The recombinant vector according to claim 7, wherein the polynucleotide encoding the fusion tag comprises the nucleotide sequence of SEQ ID NO: 7.

14. The recombinant vector of claim 1, wherein the polynucleotide encodes the fusion tag comprising the peptide comprising the amino acid sequence of SEQ ID NO: 20.

* * * * *

SEQUENCE LISTING

<160> NUMBER OF SEQ ID NOS: 41

<210> SEQ ID NO 1
<211> LENGTH: 8
<212> TYPE: PRT
<213> ORGANISM: Artificial Sequence
<220> FEATURE:
<223> OTHER INFORMATION: peptide tag domain
<220> FEATURE:
<221> NAME/KEY: VARIANT
<222> LOCATION: (3)..(3)
<223> OTHER INFORMATION: I or L
<220> FEATURE:
<221> NAME/KEY: VARIANT
<222> LOCATION: (7)..(7)
<223> OTHER INFORMATION: A or S

<400> SEQUENCE: 1

Pro Leu Xaa Asp Leu Gly Xaa Glu
1               5

<210> SEQ ID NO 2
<211> LENGTH: 53
<212> TYPE: PRT
<213> ORGANISM: Hydrogenovibrio marinus

<400> SEQUENCE: 2

Met Ala Val Gln His Ser Asn Ala Pro Leu Ile Asp Leu Gly Ala Glu
1               5                   10                  15

Met Lys Lys Gln His Lys Glu Ala Ala Pro Glu Gly Ala Ala Pro Ala
            20                  25                  30

Gln Gly Lys Ala Pro Ala Ala Glu Ala Lys Lys Glu Glu Ala Pro Lys
        35                  40                  45

Pro Lys Pro Val Val
    50

<210> SEQ ID NO 3
<211> LENGTH: 51
<212> TYPE: PRT
<213> ORGANISM: Hydrogenovibrio crunogenus

<400> SEQUENCE: 3

Met Ala Pro Leu Ile Asp Leu Gly Ala Glu Ala Lys Lys Gln Ala Gln
1               5                   10                  15

Lys Ser Ala Ala Thr Gln Ser Ala Val Pro Glu Lys Glu Ser Ala Thr
            20                  25                  30

Lys Val Ala Glu Lys Gln Lys Glu Pro Glu Glu Lys Ala Lys Pro Glu
        35                  40                  45

Pro Lys Lys
    50

<210> SEQ ID NO 4
<211> LENGTH: 57
<212> TYPE: PRT
<213> ORGANISM: Hydrogenovibrio kuenenii

<400> SEQUENCE: 4

Met Ala Gly Ile Gln His Ser Asn Ala Pro Leu Leu Asp Leu Gly Ser
1               5                   10                  15

Glu Val Lys Gly His Ala Gly Asn Ser Ser Pro Ser Ala Pro Thr
            20                  25                  30

Met Glu Ser Gln Thr Thr Thr Ser Thr Ser Val Ala Lys Ala Lys Lys
        35                  40                  45

Pro Lys Glu Pro Glu Lys Lys Val Val
    50                  55

<210> SEQ ID NO 5
<211> LENGTH: 159
<212> TYPE: DNA
<213> ORGANISM: Hydrogenovibrio marinus

<400> SEQUENCE: 5
atggctgttc aacatagcaa tgccccattg attgacttgg gcgcggaaat gaaaaaacag      60
cacaaggagg cagctcccga aggcgctgcg ccggctcaag gtaaggcacc tgccgcggaa     120
gccaaaaaag aagaagcacc taaaccaaaa cccgttgtg                            159

<210> SEQ ID NO 6
<211> LENGTH: 153
<212> TYPE: DNA
<213> ORGANISM: Hydrogenovibrio crunogenus

<400> SEQUENCE: 6
atggcaccat tgattgattt aggagcggaa gccaaaaagc aagcgcagaa atcagcggcg      60
actcagtctg cagtgcctga aaagagtcc gccactaagg ttgctgaaaa acaaaaagag     120
ccggaagaaa aagccaagcc tgagccaaaa aaa                                 153

<210> SEQ ID NO 7
<211> LENGTH: 171
<212> TYPE: DNA
<213> ORGANISM: Hydrogenovibrio kuenenii

<400> SEQUENCE: 7
atggctggca ttcagcattc gaatgctcct ctccttgatt tggggtcaga ggtaaaaggc      60
catgcaggca acagtagctc gccaagcgct ccaactatgg agtctcagac tacgacttca     120
acatcggttg caaaggctaa aaaaccaaaa gaaccggaaa agaaagttgt c              171

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
catatggctg ttcaacatag caatgcccc                                       29

<210> SEQ ID NO 9
<211> LENGTH: 54
<212> TYPE: DNA
<213> ORGANISM: Artificial Sequence
<220> FEATURE:
<223> OTHER INFORMATION: primer

<400> SEQUENCE: 9
ccatggagcc tccaccgccg ctgccacctc cgcccacaac gggttttggt ttag           54

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
catatgaaaa tcgaagaagg taaactg                                      27

<210> SEQ ID NO 11
<211> LENGTH: 50
<212> TYPE: DNA
<213> ORGANISM: Artificial Sequence
<220> FEATURE:
<223> OTHER INFORMATION: primer

<400> SEQUENCE: 11
ccatggagcc tccaccgccg ctgccacctc cgccagtctg cgcgtctttc              50

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
catatgtccc ctatactagg ttattgg                                      27

<210> SEQ ID NO 13
<211> LENGTH: 53
<212> TYPE: DNA
<213> ORGANISM: Artificial Sequence
<220> FEATURE:
<223> OTHER INFORMATION: primer

<400> SEQUENCE: 13
ccatggagcc tccaccgccg ctgccacctc cgccatccga ttttggagga tgg          53

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
ccatgggcag taaaggagaa gaactttcca ctg                               33

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
ctcgagtttg tagagctcat ccatgc                                       26

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
ccatggaaga tgccaaaaac attaag                                       26

<210> SEQ ID NO 17
<211> LENGTH: 21
<212> TYPE: DNA

```
<213> ORGANISM: Artificial Sequence
<220> FEATURE:
<223> OTHER INFORMATION: primer

<400> SEQUENCE: 17
ctcgagcacg gcgatcttgc c                                                  21

<210> SEQ ID NO 18
<211> LENGTH: 15
<212> TYPE: DNA
<213> ORGANISM: Artificial Sequence
<220> FEATURE:
<223> OTHER INFORMATION: primer

<400> SEQUENCE: 18
ccatgggtgg tggcg                                                         15

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ctcgagcttc atcactttac                                                    20

<210> SEQ ID NO 20
<211> LENGTH: 17
<212> TYPE: PRT
<213> ORGANISM: Hydrogenovibrio marinus

<400> SEQUENCE: 20

Met Ala Ala Glu Ala Lys Lys Glu Glu Ala Pro Lys Pro Lys Pro Val
1               5                   10                  15

Val

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
catatggccg cggaagccaa aaa                                                23

<210> SEQ ID NO 22
<211> LENGTH: 699
<212> TYPE: DNA
<213> ORGANISM: Desulfovibrio vulgaris

<400> SEQUENCE: 22
atgcaccacc atcatcatca cggcggcggg ggctcaacgg gaccgggtat tggtccagac         60
gaagcacttc aacggcttaa agaaggtaac gcgcgtttcg ttgcagagac gcctcggccc        120
cagaaccttt cggccagacg tctgttgaca tccatgttgg gccagacacc gttcgcgacg        180
atactgtctt gttctgattc cagagcccct gttgagctta tattcgatca aggaattggg        240
gatttattcg taattcgggt tgcaggaaac gtcgctcaaa cggatgaggt cggtactgca        300
gagtatggag tggatcactt aaatgtcccc ttgttagtag taatgggcca cacacagtgc        360
ggtgcggtta ctgctgttgt gatgcgggca gaggtgcgtg gtaacattcc cttttttggtg      420
```

```
gcccccatag tcccggcagt tatggcggta gaaaaaagat gtcccaaaac cgaccgcgct    480
gcccttgtcc ctaaagccat cgaggctaat gtctggcaag ctattgatga cacatttaga    540
cagtcaccga taatacgcgc cagagtggcg gcagggaaat tgaaggtagt gggcgccata    600
taccatattg attctggtaa ggtagaatgg ttaggagagc atcccatgca ggcgcggttg    660
ttggaatata ccagcggacc gactaaagca caccggtga                           699
```

<210> SEQ ID NO 23
<211> LENGTH: 232
<212> TYPE: PRT
<213> ORGANISM: Desulfovibrio vulgaris

<400> SEQUENCE: 23

```
Met His His His His His Gly Gly Gly Gly Ser Thr Gly Pro Gly
1               5                   10                  15

Ile Gly Pro Asp Glu Ala Leu Gln Arg Leu Lys Glu Gly Asn Ala Arg
            20                  25                  30

Phe Val Ala Glu Thr Pro Arg Pro Gln Asn Leu Ser Ala Arg Leu
        35                  40                  45

Leu Thr Ser Met Leu Gly Gln Thr Pro Phe Ala Thr Ile Leu Ser Cys
50                  55                  60

Ser Asp Ser Arg Ala Pro Val Glu Leu Ile Phe Asp Gln Gly Ile Gly
65                  70                  75                  80

Asp Leu Phe Val Ile Arg Val Ala Gly Asn Val Ala Gln Thr Asp Glu
                85                  90                  95

Val Gly Thr Ala Glu Tyr Gly Val Asp His Leu Asn Val Pro Leu Leu
            100                 105                 110

Val Val Met Gly His Thr Gln Cys Gly Ala Val Thr Ala Val Val Met
        115                 120                 125

Arg Ala Glu Val Arg Gly Asn Ile Pro Phe Leu Val Ala Pro Ile Val
130                 135                 140

Pro Ala Val Met Ala Val Glu Lys Arg Cys Pro Lys Thr Asp Arg Ala
145                 150                 155                 160

Ala Leu Val Pro Lys Ala Ile Glu Ala Asn Val Trp Gln Ala Ile Asp
                165                 170                 175

Asp Thr Phe Arg Gln Ser Pro Ile Ile Arg Ala Arg Val Ala Ala Gly
            180                 185                 190

Lys Leu Lys Val Val Gly Ala Ile Tyr His Ile Asp Ser Gly Lys Val
        195                 200                 205

Glu Trp Leu Gly Glu His Pro Met Gln Ala Arg Leu Leu Glu Tyr Thr
210                 215                 220

Ser Gly Pro Thr Lys Ala His Arg
225                 230
```

<210> SEQ ID NO 24
<211> LENGTH: 10
<212> TYPE: PRT
<213> ORGANISM: Artificial Sequence
<220> FEATURE:
<223> OTHER INFORMATION: flexible GS linker

<400> SEQUENCE: 24

```
Gly Gly Gly Gly Ser Gly Gly Gly Gly Ser
1               5                   10
```

<210> SEQ ID NO 25
<211> LENGTH: 329

<212> TYPE: PRT
<213> ORGANISM: Thiomicrospira sp. WB1

<400> SEQUENCE: 25

```
Met Asp Asp His Leu Ser Phe Ser Phe Arg Val Val Pro Trp Arg Pro
1               5                   10                  15

Phe Val Ile Ala Val Thr Leu Gly Leu Ala Trp Pro Val His Ala Glu
            20                  25                  30

Glu Pro Leu Leu Asn Leu Gly Ala Glu Ala Gln Gly Ser Ala Pro Met
        35                  40                  45

Gln Pro Asn Arg Glu Ser Asn Leu Pro Ser Asp Glu Pro Glu Val Asp
    50                  55                  60

Lys Gly Gly Met Thr Gln Lys Glu Lys Gln Ala Asn Ala Glu Asp Gln
65                  70                  75                  80

Ala Asp Lys Gln Lys Pro Pro Glu Trp Gly Tyr His Asp Glu Leu Ala
                85                  90                  95

Pro Arg His Trp Ala Glu Leu Ser Pro Arg Tyr Ala Leu Cys Gly Glu
            100                 105                 110

Gly Gln Ser Gln Ser Pro Ile Asn Leu Lys Arg Gln Gly Ala Val Gly
        115                 120                 125

Thr Thr Gly Leu Pro Gly Phe Asp Val His Tyr Arg Glu Thr Val Leu
130                 135                 140

Lys Thr Glu Phe Asp Gly Lys Arg Leu Lys Val Asn Val Pro Val Gly
145                 150                 155                 160

Ser Tyr Val Arg Leu Gln Asn Arg Arg Tyr Glu Leu Ile His Tyr Glu
                165                 170                 175

Phe His Thr Pro Ser Glu His Gln Lys Asp Gly Phe Ala Tyr Pro Ala
            180                 185                 190

Glu Leu Gln Trp Val His Lys Asp Gly Glu Gly Asn Tyr Val Asn Val
        195                 200                 205

Ala Val Leu Phe Arg Glu Gly Gln Ala Asn Glu Ala Leu Glu Thr Val
    210                 215                 220

Leu Ser Asn Leu Pro Gly Glu Met Asn Gln Glu Arg Val Asn Glu Gly
225                 230                 235                 240

Val Lys Leu Pro Ala Thr Asp Phe Ile Pro Pro Ser Arg Lys Phe Tyr
                245                 250                 255

Lys Tyr His Gly Ser Leu Ala His Pro Pro Cys Thr Glu Ser Val Tyr
            260                 265                 270

Trp Met Val Phe Asp Gln Pro Leu Glu Ala Ser Val Ser Gln Leu Thr
        275                 280                 285

Arg Leu Gln Glu Tyr Leu Gly Asn Asn Ala Arg Pro Val Gln Pro Leu
    290                 295                 300

Lys Ala Arg Thr Leu Leu Lys Ser Trp Pro Asp Glu Ser Glu Gln Ala
305                 310                 315                 320

Ala Asp Tyr Pro Phe Tyr Tyr Thr Pro
                325
```

<210> SEQ ID NO 26
<211> LENGTH: 337
<212> TYPE: PRT
<213> ORGANISM: Hydrogenovibrio halophilus

<400> SEQUENCE: 26

```
Met Thr Leu Ser Trp Thr Arg Leu Ser Val Tyr Arg Ser Ala Arg Ser
1               5                   10                  15
```

```
Asp Trp Leu Ala Leu Ser Leu Val Gly Leu Leu Gly Phe Ser Gly Gly
             20                  25                  30

Val Ala Ala Glu Glu Ser Leu Leu Asn Leu Gly Ala Glu Ala Gln Gly
         35                  40                  45

Gln Ser Gln Gly Glu Glu Arg Gly Asp Glu Asn Asp Pro Ser Arg Asp
     50                  55                  60

Gln Pro Glu Val Asp Lys Gly Gly Met Pro Asn Asp Gly Lys Asn Gly
 65                  70                  75                  80

Asp Ala Asp Gln Asp Gln Lys Asn Ala Glu Asn Glu Ala Pro Pro Glu
                 85                  90                  95

Trp Gly Tyr His Asp Asp Lys Ala Pro Arg His Trp Ala Glu Leu Ser
            100                 105                 110

Glu Ala Tyr Ala Leu Cys Gly Ser Gly Gln Ala Gln Ser Pro Ile Asp
        115                 120                 125

Ile Lys Arg Gln Gly Ala Val Gly Thr Thr Gly Leu Pro Gly Phe Asp
    130                 135                 140

Ile His Tyr Arg Glu Thr Val Leu Lys Thr Glu Phe Asp Gly Lys Arg
145                 150                 155                 160

Leu Lys Val Asn Ile Pro Val Gly Ser Tyr Ile Arg Leu Gln Asn Arg
                165                 170                 175

Arg Tyr Glu Leu Thr His Tyr Glu Phe His Thr Pro Ser Glu His His
            180                 185                 190

Lys Asp Gly Phe Ala Tyr Pro Ala Glu Leu Gln Leu Val His Lys Asp
        195                 200                 205

Gly Glu Gly Asn His Val Val Ala Val Leu Phe Arg Glu Gly Asp
    210                 215                 220

Glu His Glu His Leu Ala Thr Val Leu Glu Asn Leu Pro Gly Glu Ile
225                 230                 235                 240

Asn Gln Glu Lys Val Asn Gln Ser Val Lys Leu Pro Pro Ala Asn Phe
                245                 250                 255

Ile Pro Gly Ala Arg Lys Phe Tyr Lys Tyr His Gly Ser Leu Thr His
            260                 265                 270

Pro Pro Cys Asp Glu Gly Val Tyr Trp Met Val Phe Asp Gln Pro Leu
        275                 280                 285

Glu Ala Ser Val Ser Gln Leu Gln Arg Leu Gln Asp Tyr Leu Gly Asn
    290                 295                 300

Asn Ala Arg Pro Val Gln Pro Met Lys Ala Arg Thr Leu Leu Lys Ser
305                 310                 315                 320

Trp Pro Asp Gln Ser Gly Arg Ala Ala Asp Tyr Glu Phe Tyr Tyr Thr
                325                 330                 335

Pro

<210> SEQ ID NO 27
<211> LENGTH: 324
<212> TYPE: PRT
<213> ORGANISM: Thiomicrospira sp. CG2_30_44_34

<400> SEQUENCE: 27

Met Arg Asn Gly Leu Ile Ile Thr Ile Leu Leu Gly Leu Leu Leu Pro
1               5                   10                  15

Phe Tyr Ala Ala Asn Ala Ser Asn Glu Pro Leu Ile Asp Leu Lys Ser
             20                  25                  30

Glu Ala Lys Lys Tyr Gly Glu Val Val Glu Glu Lys Gln Val Ala Glu
         35                  40                  45
```

Pro Thr Arg Ser Gln Pro Lys Pro Ser Glu Lys Gln Glu Pro Ala His
            50                  55                  60

Gln Gln Ala Ala Ala Lys Thr Glu Thr Ala Thr Lys Pro His Ser Thr
 65                  70                  75                  80

Pro Glu His Pro Pro His Trp Thr Tyr Ser Gly Glu Thr Gly Pro Arg
                85                  90                  95

His Trp Gly Glu Leu Ser Asp Gln Phe Ser Leu Cys Gln Thr Gly Lys
            100                 105                 110

Asn Gln Ser Pro Ile Asn Leu Lys Met Gln Gln Ala Val Gly Thr Thr
        115                 120                 125

Ser Leu Pro Gly Phe Asp Val Tyr Tyr Arg Glu Thr Ala Leu Lys Met
130                 135                 140

Val Asn Asn Gly His Thr Leu Gln Val Asn Ile Pro Leu Gly Ser Tyr
145                 150                 155                 160

Ile Glu Ile Asp Gly Arg Arg Phe Glu Leu Leu Gln Tyr His Phe His
                165                 170                 175

Thr Pro Ser Glu His Gln Arg Asp Gly Phe Asn Tyr Pro Met Glu Met
            180                 185                 190

His Leu Val His Lys Asp Ala Asp Gly Asn Leu Ala Val Ile Gly Val
        195                 200                 205

Leu Phe Gln Glu Gly Glu Asn Glu Ala Leu Ala Gln Met Leu Pro
210                 215                 220

Val Leu Pro Gln Val Lys Asp Lys Val Asp Ile His Glu Trp Ile Lys
225                 230                 235                 240

Ile His Pro Ala Ala Phe Phe Pro Ala Asp Lys Lys Phe Tyr Lys Tyr
                245                 250                 255

Ser Gly Ser Leu Thr Thr Pro Pro Cys Ser Glu Gly Val Tyr Trp Met
            260                 265                 270

Val Phe Lys Asn Pro Ile Gln Ala Ser Val Met Gln Leu Lys Gln Leu
        275                 280                 285

His Asp Tyr Leu Gly Ser Asn Ala Arg Pro Val Asn Pro His Tyr Ala
290                 295                 300

Arg Ser Leu Leu Lys Ser Trp Gln Asp Ile Pro Leu Gln Asn Arg Val
305                 310                 315                 320

Tyr Glu Phe Tyr

<210> SEQ ID NO 28
<211> LENGTH: 285
<212> TYPE: PRT
<213> ORGANISM: Piscirickettsiaceae bacterium
      CG18_big_fil_WC_8_21_14_2_50_44_103

<400> SEQUENCE: 28

Met Arg Asn Gly Leu Ile Ile Thr Ile Leu Leu Gly Leu Leu Leu Pro
 1               5                  10                  15

Phe Tyr Ala Ala Asn Ala Ser Asn Glu Pro Leu Ile Asp Leu Lys Ser
            20                  25                  30

Glu Ala Lys Lys Tyr Gly Glu Val Val Glu Lys Gln Val Ala Glu
        35                  40                  45

Pro Thr Arg Ser Gln Pro Lys Pro Ser Glu Lys Gln Glu Pro Ala His
    50                  55                  60

Gln Gln Ala Ala Ala Lys Thr Glu Thr Ala Thr Lys Pro His Ser Thr
 65                  70                  75                  80

Pro Glu His Pro Pro His Trp Thr Tyr Ser Gly Glu Thr Gly Pro Arg
                85                  90                  95

```
His Trp Gly Glu Leu Ser Asp Gln Phe Ser Leu Cys Gln Thr Gly Lys
            100                 105                 110

Asn Gln Ser Pro Ile Asn Leu Lys Met Gln Gln Ala Val Gly Thr Thr
        115                 120                 125

Ser Leu Pro Gly Phe Asp Val Tyr Tyr Arg Glu Thr Ala Leu Lys Met
130                 135                 140

Val Asn Asn Gly His Thr Leu Gln Val Asn Ile Pro Leu Gly Ser Tyr
145                 150                 155                 160

Ile Glu Ile Asp Gly Arg Arg Phe Glu Leu Leu Gln Tyr His Phe His
                165                 170                 175

Thr Pro Ser Glu His Gln Arg Asp Gly Phe Asn Tyr Pro Met Glu Met
            180                 185                 190

His Leu Val His Lys Asp Ala Asp Gly Asn Leu Ala Val Ile Gly Val
        195                 200                 205

Leu Phe Gln Glu Gly Glu Asn Glu Ala Leu Ala Gln Met Leu Pro
210                 215                 220

Val Leu Pro Gln Val Lys Asp Lys Val Asp Ile His Glu Trp Ile Lys
225                 230                 235                 240

Ile His Pro Ala Ala Phe Phe Pro Ala Asp Lys Lys Phe Tyr Lys Tyr
                245                 250                 255

Ser Gly Ser Leu Thr Thr Pro Pro Cys Ser Glu Gly Val Tyr Trp Met
            260                 265                 270

Val Phe Lys Asn Pro Ile Gln Ala Ser Val Met Gln Leu
        275                 280                 285

<210> SEQ ID NO 29
<211> LENGTH: 315
<212> TYPE: PRT
<213> ORGANISM: Hydrogenovibrio crunogena XCL-2

<400> SEQUENCE: 29

Met Lys Lys Arg Phe Ser Phe Ile Phe Ile Phe Leu Val Ala Leu Pro
1               5                   10                  15

Leu Tyr Ser Ala Asn Asn Val Ala Ala Pro Leu Ile Asp Leu Gly Ala
            20                  25                  30

Glu Ala Lys Lys Gln Ala Gln Lys Ser Ala Ala Thr Gln Ser Ala Val
        35                  40                  45

Pro Glu Lys Glu Ser Ala Thr Lys Val Ala Glu Lys Gln Lys Glu Pro
    50                  55                  60

Glu Glu Lys Ala Lys Pro Glu Pro Lys Lys Pro Pro His Trp Gly Tyr
65                  70                  75                  80

Phe Gly Glu Glu Gly Pro Gln Tyr Trp Gly Glu Leu Ala Pro Glu Phe
                85                  90                  95

Ser Thr Cys Lys Thr Gly Lys Asn Gln Ser Pro Ile Asn Leu Lys Pro
            100                 105                 110

Gln Thr Ala Val Gly Thr Thr Ser Leu Pro Gly Phe Asp Val Tyr Tyr
        115                 120                 125

Arg Glu Thr Ala Leu Lys Leu Ile Asn Asn Gly His Thr Leu Gln Val
    130                 135                 140

Asn Ile Pro Leu Gly Ser Tyr Ile Lys Ile Asn Gly His Arg Tyr Glu
145                 150                 155                 160

Leu Leu Gln Tyr His Phe His Thr Pro Ser Glu His Gln Arg Asp Gly
                165                 170                 175

Phe Asn Tyr Pro Met Glu Met His Leu Val His Lys Asp Gly Asp Gly
```

```
            180                 185                 190
Asn Leu Ala Val Ile Ala Ile Leu Phe Gln Glu Gly Glu Asn Glu
        195                 200                 205

Thr Leu Ala Lys Leu Met Ser Phe Leu Pro Gln Thr Leu Lys Lys Gln
210                 215                 220

Glu Ile His Glu Ser Val Lys Ile His Pro Ala Lys Phe Phe Pro Ala
225                 230                 235                 240

Asp Lys Lys Phe Tyr Lys Tyr Ser Gly Ser Leu Thr Thr Pro Pro Cys
                245                 250                 255

Ser Glu Gly Val Tyr Trp Met Val Phe Lys Gln Pro Ile Gln Ala Ser
                260                 265                 270

Val Thr Gln Leu Glu Lys Met His Glu Tyr Leu Gly Ser Asn Ala Arg
            275                 280                 285

Pro Val Gln Arg Gln Asn Ala Arg Thr Leu Leu Lys Ser Trp Pro Asp
            290                 295                 300

Arg Asn Arg Ala Asn Thr Val Tyr Glu Phe Tyr
305                 310                 315

<210> SEQ ID NO 30
<211> LENGTH: 329
<212> TYPE: PRT
<213> ORGANISM: Thiomicrospira sp. XS5

<400> SEQUENCE: 30

Met Asn Thr Arg Ser Ser Phe Leu Met Leu Leu Gly Cys Leu Val Cys
1               5                   10                  15

Leu Pro Leu Tyr Ala Ala Asp Ser Asn Val Pro Pro Leu Ile Asp Leu
                20                  25                  30

Gly Ala Glu Ala Lys Lys Gln Ala Glu Lys Gln Lys Asn Ile Thr Val
            35                  40                  45

Ser Gln Pro Lys Pro Ala Val Lys Ser Lys Pro Lys Ala Thr Thr Gln
50                  55                  60

Asp Ala Ser Glu Ala Lys Val Ala Ala Lys Pro Lys Ala Ala Lys Leu
65                  70                  75                  80

Ala Pro Glu Pro Val Glu Thr Lys Pro Val Ala Trp Ser Tyr Phe Gly
                85                  90                  95

Asp Asp Gly Pro Gln Asn Trp Gly Gln Leu Ser Thr Ala Tyr Ala Thr
            100                 105                 110

Cys Lys Ala Gly Lys Asn Gln Ser Pro Ile Asn Phe Lys Arg Asp Asp
        115                 120                 125

Ala Val Gly Thr Thr Ser Leu Asp Gly Phe Asp Val Tyr Tyr Arg Lys
    130                 135                 140

Ser Ile Leu Lys Met Ile Asn Asp Gly His Val Leu Lys Val Glu Val
145                 150                 155                 160

Pro Leu Gly Ser Tyr Ile Met Leu Asn Gly Gln Arg Tyr Glu Leu Thr
                165                 170                 175

Glu Tyr Glu Phe His Thr Pro Ser Glu His Gln Ile Asp Gly Phe Ser
            180                 185                 190

Tyr Pro Met Glu Met Gln Leu Val His Lys Asn Gly Asp Gly His Tyr
        195                 200                 205

Val Val Val Ser Ile Leu Phe Gln Glu Gly Glu Ala Asn Glu Ala Leu
    210                 215                 220

Ala Ala Phe Leu Asp Arg Leu Pro Lys Gln Leu Asn Lys Leu Asp Val
225                 230                 235                 240
```

His Asp Lys Val Leu Val His Pro Ala Lys Ala Phe Phe Pro Ala Asp
            245                 250                 255

Lys Arg Phe Tyr Lys Tyr Ser Gly Ser Met Thr Gln Pro Pro Cys Asp
        260                 265                 270

Glu Gly Val Tyr Trp Met Val Phe Lys Gln Pro Val Glu Ala Ser Ala
    275                 280                 285

Ala Gln Leu Gln Gln Met Lys Glu Tyr Leu Gly Thr Asn Ala Arg Pro
290                 295                 300

Val Gln Pro Leu Asn Ser Arg Thr Pro Leu Lys Ser Trp Pro Asp Arg
305                 310                 315                 320

Gln Ala Gln Glu Ser Phe Tyr Leu Tyr
            325

<210> SEQ ID NO 31
<211> LENGTH: 329
<212> TYPE: PRT
<213> ORGANISM: Thiomicrospira sp. MA2-6

<400> SEQUENCE: 31

Met Asn Thr Arg Ser Ser Phe Leu Met Leu Leu Gly Cys Leu Val Cys
1               5                   10                  15

Leu Pro Leu Tyr Ala Ala Asp Ser Asn Val Pro Pro Leu Ile Asp Leu
            20                  25                  30

Gly Ala Glu Ala Lys Lys Gln Ala Glu Lys Gln Lys Ile Ala Val
        35                  40                  45

Ser Gln Pro Lys Pro Ala Glu Thr Ser Gln Pro Lys Ala Gln Ala Asp
    50                  55                  60

Asp Ala Asp Lys Ala Lys Val Ala Ala Lys Pro Glu Ala Ala Lys Pro
65                  70                  75                  80

Ala Ala Glu Pro Ala Glu Thr Lys Pro Val Ala Trp Ser Tyr Phe Gly
            85                  90                  95

Asp Asp Gly Pro Gln Asn Trp Gly Gln Leu Ser Thr Ala Tyr Ala Thr
            100                 105                 110

Cys Lys Ala Gly Lys Asn Gln Ser Pro Ile Asn Phe Lys Arg Asp Asp
        115                 120                 125

Ala Val Gly Thr Thr Ser Leu Asn Gly Phe Asp Val Tyr Tyr Arg Lys
    130                 135                 140

Ser Ile Leu Lys Met Ile Asn Asp Gly His Val Leu Lys Val Glu Val
145                 150                 155                 160

Pro Leu Gly Ser Tyr Ile Met Leu Asn Gly Gln Arg Tyr Glu Leu Met
            165                 170                 175

Glu Tyr Glu Phe His Thr Pro Ser Glu His Gln Ile Asp Gly Phe Ser
            180                 185                 190

Tyr Pro Met Glu Met Gln Leu Val His Lys Asp Gly Asn Gly Asp Tyr
        195                 200                 205

Ala Val Val Ser Ile Leu Phe Gln Glu Gly Ala Glu Asn Glu Ala Leu
    210                 215                 220

Ala Ala Phe Leu Asp Arg Leu Pro Lys Gln Leu Asn Lys Leu Asp Val
225                 230                 235                 240

His Asp Lys Val Leu Val His Pro Ala Lys Ala Phe Phe Pro Val Asp
            245                 250                 255

Lys Arg Phe Tyr Lys Tyr Ser Gly Ser Met Thr Gln Pro Pro Cys Asp
        260                 265                 270

Glu Gly Val Tyr Trp Met Val Phe Lys Gln Pro Val Glu Ala Ser Ala
    275                 280                 285

```
Ala Gln Leu Gln Gln Met Thr Glu Tyr Leu Gly Thr Asn Ala Arg Pro
        290                 295                 300

Val Gln Pro Leu Asn Ala Arg Thr Pro Leu Lys Ser Trp Pro Asp Arg
305                 310                 315                 320

Gln Ala Gln Glu Ser Phe Tyr Leu Tyr
                325

<210> SEQ ID NO 32
<211> LENGTH: 323
<212> TYPE: PRT
<213> ORGANISM: Hydrogenovibrio marinus

<400> SEQUENCE: 32

Met Lys Ala Leu Lys Arg Leu Leu Ile Ala Phe Ile Ser Phe Gly Val
1               5                   10                  15

Cys Leu Val Ala Pro Gln Gly Trp Ser Ala Ala Val Gln His Ser Asn
            20                  25                  30

Ala Pro Leu Ile Asp Leu Gly Ala Glu Met Lys Lys Gln His Lys Glu
        35                  40                  45

Ala Ala Pro Glu Gly Ala Ala Pro Ala Gln Gly Lys Ala Pro Ala Ala
    50                  55                  60

Glu Ala Lys Lys Glu Glu Ala Pro Lys Pro Lys Pro Val Val His Asn
65                  70                  75                  80

Pro His Trp Ser Tyr Ser Gly Glu Glu Gly Pro Asp His Trp Gly Asp
                85                  90                  95

Leu Ser Pro Asp Tyr Ala Thr Cys Lys Thr Gly Lys Asn Gln Ser Pro
            100                 105                 110

Ile Asn Leu Met Ala Asp Asp Ala Val Gly Thr Thr Ser Leu Pro Gly
        115                 120                 125

Phe Asp Val His Tyr Arg Asp Thr Val Leu Lys Val Ile Asn Asn Gly
130                 135                 140

His Thr Leu Gln Ala Asn Val Pro Leu Gly Ser Tyr Ile Lys Ile Lys
145                 150                 155                 160

Asn Gln Arg Tyr Glu Leu Leu Gln Tyr His Phe His Thr Pro Ser Glu
                165                 170                 175

His Gln Leu Asn Gly Phe Asn Tyr Pro Met Glu Leu His Leu Val His
            180                 185                 190

Arg Asp Gly Arg Gly His Tyr Leu Val Ile Gly Ile Leu Phe Arg Glu
        195                 200                 205

Gly Lys Glu Asn Asp Ala Leu Gln Thr Ile Leu Asn His Leu Pro Lys
    210                 215                 220

Lys Val Gly Lys Gln Glu Ile Phe Asn Gly Ile Glu Phe Asn Pro Asn
225                 230                 235                 240

Val Phe Phe Pro Glu Ser Lys Lys Phe Phe Lys Tyr Ser Gly Ser Leu
                245                 250                 255

Thr Thr Pro Pro Cys Thr Glu Gly Val Tyr Trp Met Val Phe Lys Gln
            260                 265                 270

Pro Ile Glu Ala Ser Ala Glu Gln Leu Glu Lys Met Asn Glu Leu Met
        275                 280                 285

Gly Ala Asn Ala Arg Pro Val Gln Asp Leu Glu Ala Arg Ser Leu Leu
    290                 295                 300

Lys Ser Trp Ser Asn Pro Lys Asn Asp Ser Gln Asp His Arg Tyr Tyr
305                 310                 315                 320

Gln Tyr Tyr
```

<210> SEQ ID NO 33
<211> LENGTH: 326
<212> TYPE: PRT
<213> ORGANISM: Hydrogenovibrio kuenenii

<400> SEQUENCE: 33

Met Lys Thr Leu Lys Thr Leu Phe Ile Ala Phe Ile Ser Ala Gly Ile
1               5                   10                  15

Phe Phe Val Thr Pro Glu Gly Trp Ser Ala Gly Ile Gln His Ser Asn
            20                  25                  30

Ala Pro Leu Leu Asp Leu Gly Ser Glu Val Lys Gly His Ala Gly Asn
        35                  40                  45

Ser Ser Ser Pro Ser Ala Pro Thr Met Glu Ser Gln Thr Thr Thr Ser
    50                  55                  60

Thr Ser Val Ala Lys Ala Lys Lys Pro Lys Glu Pro Glu Lys Lys Val
65                  70                  75                  80

Val His Asn Pro His Trp Ser Tyr Met Gly Lys Glu Gly Pro Asp Tyr
                85                  90                  95

Trp Gly Asp Leu Ser Pro Asp Tyr Ala Leu Cys Lys Thr Gly Lys Asn
            100                 105                 110

Gln Ser Pro Val Asn Leu Met Thr Asp Ala Ala Val Gly Thr Thr Ser
        115                 120                 125

Leu Pro Gly Phe Asp Val His Tyr Arg Asp Thr Val Leu Lys Val Ile
    130                 135                 140

Asn Asn Gly His Thr Leu Gln Val Asn Val Pro Leu Gly Ser Tyr Ile
145                 150                 155                 160

Lys Ile Asn Asn His Arg Tyr Glu Leu Met Gln Tyr His Phe His Thr
                165                 170                 175

Pro Ser Glu His Gln Leu Asn Gly Phe Asn Tyr Pro Met Glu Leu His
            180                 185                 190

Leu Val His Arg Asp Gly Arg Gly His Tyr Ile Val Ile Gly Ile Leu
        195                 200                 205

Phe Arg Glu Gly Lys Glu Asn Asp Ala Leu Gln Thr Ile Leu Asp His
    210                 215                 220

Leu Pro Lys Lys Lys Gly Lys Gln Glu Ile Phe Ser Gly Val Thr Phe
225                 230                 235                 240

Asn Pro Asn Val Phe Phe Pro Glu Ser Lys Lys Phe Phe Lys Tyr Ser
                245                 250                 255

Gly Ser Leu Thr Thr Pro Pro Cys Ser Glu Gly Val Tyr Trp Met Val
            260                 265                 270

Phe Gln Gln Pro Val Glu Ala Ser Ala Glu Gln Leu Glu Lys Met Asn
        275                 280                 285

Glu Leu Met Gly Ser Asn Ala Arg Pro Val Gln Asn Leu Asn Ala Arg
    290                 295                 300

Ser Leu Leu Lys Ser Trp Asn Asp Pro Lys Gln Asn Gly Gln Asp Asn
305                 310                 315                 320

Arg Tyr Tyr Gln Phe Tyr
                325

<210> SEQ ID NO 34
<211> LENGTH: 307
<212> TYPE: PRT
<213> ORGANISM: Thiomicrospira milos T1

<400> SEQUENCE: 34

```
Met Gln Thr Trp Ser Ala Pro Val Gln His Thr Asn Gln Pro Leu Leu
1               5                   10                  15

Asn Leu Gly Ala Glu Met Lys Val Asp Ala Gly His Ala Pro Asn Ser
            20                  25                  30

Lys Ala Ser Pro Ala Gln Pro Glu Lys Ala Ile Glu Gln Ser Lys Gln
        35                  40                  45

Leu Lys Lys Pro Ala Glu Thr Ser Lys Lys Ile Val His Asn Pro
50                  55                  60

His Trp Ser Tyr Ile Gly Lys Glu Gly Pro Asp His Trp Gly Asp Leu
65                  70                  75                  80

Ser Pro Asp Tyr Ser Leu Cys Lys Thr Gly Lys Asn Gln Ser Pro Ile
                85                  90                  95

Asn Leu Met Ser Asp Asn Ser Val Gly Thr Thr Asn Leu Pro Gly Phe
            100                 105                 110

Asp Val His Tyr Arg Asp Thr Ile Leu Lys Val Ile Asn Asn Gly His
        115                 120                 125

Thr Leu Gln Val Asn Val Pro Leu Gly Ser Tyr Ile Thr Ile Gln Asn
130                 135                 140

His Arg Tyr Glu Leu Leu Gln Tyr His Phe His Thr Pro Ser Glu His
145                 150                 155                 160

Gln Leu Asp Gly Phe Asn Tyr Pro Met Glu Leu His Leu Val His Arg
                165                 170                 175

Asp Gly Arg Gly Asn Tyr Val Val Ile Gly Ile Leu Phe Arg Glu Gly
            180                 185                 190

Lys Glu Asn Asp Ala Leu Gln Thr Leu Leu Asp His Leu Pro Lys Lys
        195                 200                 205

Arg Asn Lys Gln Ala Met Phe Asn Gly Ile Glu Phe Asn Pro Asn Val
210                 215                 220

Phe Phe Pro Met Asn Lys Gln Phe Phe Lys Tyr Ser Gly Ser Phe Thr
225                 230                 235                 240

Thr Pro Pro Cys Thr Glu Gly Val Tyr Trp Met Val Phe Lys Gln Pro
                245                 250                 255

Leu Glu Ala Ser Ala Glu Gln Leu Glu Lys Met Asn Glu Ile Leu Gly
            260                 265                 270

Ser Asn Asn Arg Pro Val Gln Lys Leu Gly Ala Arg Ser Leu Leu Lys
        275                 280                 285

Ser Trp His Lys Pro Lys His Gln Asp Gly Met Asp Asn Arg Tyr Tyr
290                 295                 300

Gln Tyr Tyr
305

<210> SEQ ID NO 35
<211> LENGTH: 324
<212> TYPE: PRT
<213> ORGANISM: Thiomicrospira milos T2

<400> SEQUENCE: 35

Met Lys Lys Leu Ala Leu Lys Thr Leu Leu Ile Ala Leu Ser Leu Ser
1               5                   10                  15

Ser Thr Gln Val Leu Ser Glu Ser His Gly Thr Glu Lys Ser His Ala
            20                  25                  30

Pro Leu Val Asp Leu Gly Ala Glu Leu Lys Ala Lys Thr Gly Ser His
        35                  40                  45

Asp Gly Ser His Ser Thr Ser His Ser Pro Lys Ala Glu Pro Ala Gln
```

```
            50                  55                  60
Ser His Asn Lys Glu Thr Gln Asn Thr Ala Lys His Asp Met Glu Lys
 65                  70                  75                  80

Glu His His Ala Val His Trp Gly Tyr Thr Gly Glu Gly Gly Pro Arg
                85                  90                  95

His Trp Gly Asp Leu Ala Pro Glu Asn Ile Ser Cys Lys Ile Gly Lys
               100                 105                 110

Asn Gln Ser Pro Ile Asp Leu Arg Asp Lys Ala Ala Val Gly Thr Thr
           115                 120                 125

Gly Leu Pro Gln Leu Asp Ile His Tyr Arg Asp Val Pro Leu Lys Ile
       130                 135                 140

Val Asn Asn Gly His Thr Leu Gln Val Asn Tyr Pro Leu Gly Ser Tyr
145                 150                 155                 160

Ile Lys Val Gly Gly His Arg Tyr Glu Leu Leu Gln Phe His Phe His
                165                 170                 175

Thr Pro Ser Glu His Lys Lys Glu Gly Phe Asn Tyr Pro Met Glu Ala
            180                 185                 190

His Leu Val His Lys Asp Gly Asp Gly Asn Leu Ala Val Ile Gly Val
        195                 200                 205

Ile Phe Gln Glu Gly Glu Asn Pro Gln Val Gln Thr Leu Leu Asp
    210                 215                 220

Asn Leu Pro Lys Thr Ile Gly Lys Gln Glu Ile His Arg Asn Ala Ser
225                 230                 235                 240

Leu Asn Pro Val Met Phe Phe Pro Gly Asn Thr Glu Phe Tyr Lys Tyr
                245                 250                 255

Ser Gly Ser Leu Thr Thr Pro Pro Cys Ser Glu Gly Val Tyr Trp Met
            260                 265                 270

Val Phe Lys His Pro Ile Glu Ala Ser Ala Glu Gln Leu Glu Ala Met
        275                 280                 285

Asn Glu Val Leu Gly Glu Asn Ala Arg Pro Thr Gln Pro Val Asn Ser
    290                 295                 300

Arg Ala Met Leu Lys Ser Trp Ala Glu Gln Leu Gln Glu Pro Ser Leu
305                 310                 315                 320

Tyr Glu Phe Tyr

<210> SEQ ID NO 36
<211> LENGTH: 321
<212> TYPE: PRT
<213> ORGANISM: Thiomicrospira sp. Kp2

<400> SEQUENCE: 36

Met Lys His Pro Val Leu Lys Ser Leu Ile Val Ala Leu Gly Leu Cys
 1               5                  10                  15

Ala Leu Pro Ala Met Ser Gln Thr His Glu Thr Pro Lys Glu Pro Leu
                20                  25                  30

Val Asp Leu Gly Ala Glu Ile Lys Ala Lys Thr Gly Lys Asp Asn Leu
            35                  40                  45

Ala Lys Pro Glu Val Thr Ser Ser Thr Pro Lys Val Ile Glu Lys Lys
        50                  55                  60

Ser Glu Pro Lys Val Glu Pro Pro Lys Val Gln Glu His Lys Pro
 65                  70                  75                  80

His Trp Gly Tyr Ser Gly Glu Ser Gly Pro Lys His Trp Gly Leu
                85                  90                  95

Ala Pro Glu Asn Ile Gln Cys Lys Val Gly Lys Asn Gln Ser Pro Ile
```

```
                100                 105                 110
Asn Leu Lys Asp Lys Ala Gly Val Gly Thr Met Gly Leu Pro Gln Leu
            115                 120                 125

Asp Ile His Tyr Arg Asp Val Pro Leu Lys Ile Val Asn Asn Gly His
130                 135                 140

Thr Val Gln Val Asn Tyr Pro Leu Gly Ser Tyr Ile Lys Leu Ala Gly
145                 150                 155                 160

His Arg Tyr Glu Leu Leu Gln Phe His Phe His Thr Pro Ser Glu His
                165                 170                 175

Gln Lys Asp Gly Phe Asn Tyr Pro Met Glu Val His Leu Val His Lys
            180                 185                 190

Asp Gly Asp Gly Asn Leu Ala Val Met Gly Val Ile Phe Gln Glu Gly
195                 200                 205

Glu Glu Asn Pro Glu Ile Gln Thr Leu Leu Ser Asn Leu Pro Lys Glu
            210                 215                 220

Ile Gly Lys Glu Glu Ile Arg Arg Gly Ala Ser Ile Asn Pro Val Met
225                 230                 235                 240

Phe Ile Pro Gly Asn Thr Glu Phe Tyr Lys Tyr Ser Gly Ser Leu Thr
                245                 250                 255

Thr Pro Pro Cys Ser Glu Gly Val Tyr Trp Met Val Phe Lys Asn Pro
            260                 265                 270

Ile Glu Ala Ser Ile Glu Gln Ile Gln Gln Leu Asn Glu Val Met Gly
            275                 280                 285

Glu Asn Ala Arg Pro Val Gln Glu Ile Asn Ser Arg Thr Leu Leu Lys
            290                 295                 300

Ser Trp Ser Glu Gln Leu Leu Glu Gln Glu Ala Pro Arg Tyr Glu Phe
305                 310                 315                 320

Tyr

<210> SEQ ID NO 37
<211> LENGTH: 308
<212> TYPE: PRT
<213> ORGANISM: Thiomicrorhabdus chilensis

<400> SEQUENCE: 37

Met Phe Phe Pro Ala Val Asn Ser Ala Trp Ala Ala Glu Lys Ala Asp
1               5                   10                  15

Lys Pro Leu Val Asp Leu Gly Ala Glu Leu Ala Lys Ile Lys Lys Thr
            20                  25                  30

Glu Gln Pro Glu Asp Asp Lys Lys Pro Val Glu Asn Lys Glu Thr
        35                  40                  45

Ser Ala Ser Asp Glu Ala Lys Ile Asp Glu Lys Ala Ala Lys Asn Glu
50                  55                  60

Ser Ser His Ala Val His Trp Ser Tyr Ser Gly Glu Thr Gly Pro Arg
65                  70                  75                  80

Phe Trp Gly Glu Leu Thr Pro Glu Asn Gln Thr Cys Lys Thr Gly Arg
                85                  90                  95

Asn Gln Ser Pro Ile Asp Leu Arg Asp Ala Ala Ala Ile Gly Thr Gln
            100                 105                 110

Gly Leu Pro Gly Leu Asp Ile Val Tyr Arg Asp Val Pro Leu Lys Ile
            115                 120                 125

Val Asn Asn Gly His Ser Val Gln Val Asn Tyr Pro Leu Gly Ser Tyr
130                 135                 140

Ile Lys Leu Gly Asn His Arg Tyr Glu Leu Leu Gln Tyr His Phe His
```

```
145                 150                 155                 160

Thr Pro Ser Glu His His Lys Glu Gly Phe Ala Tyr Pro Met Glu Met
                165                 170                 175

His Phe Val His Lys Asp Gly Asp Gly Asn Leu Ala Val Leu Gly Val
                180                 185                 190

Leu Phe Gln Glu Gly Glu Thr Asn Pro Tyr Leu Asn Gly Ile Leu Lys
                195                 200                 205

Arg Leu Pro Lys Glu Val Gly Lys Gln Glu Ile Tyr Glu Asp Leu Lys
                210                 215                 220

Leu Asn Pro Val Asn Phe Leu Pro Ala Asn Thr Glu Phe Tyr Lys Tyr
225                 230                 235                 240

Ser Gly Ser Leu Thr Thr Pro Pro Cys Ser Glu Gly Val Tyr Trp Val
                245                 250                 255

Val Phe Lys His Pro Ile Glu Ala Ser Ala Arg Gln Ile Gln Gln Leu
                260                 265                 270

Asn Glu Leu Met Gly Asp Asn Ala Arg Pro Ile Gln Pro Glu Phe Ala
                275                 280                 285

Arg His Leu Leu Lys Ser Trp Met Glu Pro Asp Asn Asp Arg Gln Leu
                290                 295                 300

Tyr Glu Phe Tyr
305

<210> SEQ ID NO 38
<211> LENGTH: 325
<212> TYPE: PRT
<213> ORGANISM: Thiomicrorhabdus arctica

<400> SEQUENCE: 38

Met Asn Lys Pro Val Leu Trp Leu Leu Ser Ala Ala Leu Phe Phe Ser
1               5                   10                  15

Gly Ser Leu Val Phe Ala Ala Asp Ala Gln Asn Val Thr Lys Leu Thr
                20                  25                  30

His Glu Ser Lys Pro Leu Leu Asp Leu Gly Ala Glu Leu Asp Ser Ser
                35                  40                  45

Arg Pro Lys Val Lys Lys Ser Val Ala Arg Lys Ala Ala Pro His Ala
50                  55                  60

Pro Val Ala Lys Gln Thr Ser Thr Ala Ser Thr Pro Ala Val Gly Ala
65                  70                  75                  80

Ile Gly Asn Asn Thr Ile His Trp Gly Tyr Thr Gly Ala Ser Gly Pro
                85                  90                  95

Gln His Trp Gly Asp Leu Ala Pro Glu Asn Ile Met Cys Lys Ile Gly
                100                 105                 110

Lys Asn Gln Ser Pro Ile Asp Leu Arg Asp Asn Ala Ala Val Gly Thr
                115                 120                 125

Ile Gly Leu Pro Gln Leu Asp Val Val Tyr Gln Asn Val Pro Leu Lys
130                 135                 140

Val Ile Asn Asn Gly His Thr Val Gln Val Asn Tyr Pro Leu Gly Ser
145                 150                 155                 160

Tyr Ile Lys Val Gly Gly His Arg Tyr Glu Leu Leu Gln Phe His Phe
                165                 170                 175

His Thr Pro Ser Glu His Lys Lys Glu Gly Phe Asn Tyr Pro Met Glu
                180                 185                 190

Met His Leu Val His Lys Asp Gly Asp Gly His Leu Ala Val Met Ser
                195                 200                 205
```

```
Ile Leu Phe Gln Glu Gly Glu Asn Glu Thr Leu Asp Ala Leu Leu
    210                 215                 220

Ala Asn Leu Pro Arg Asp Val Gly Lys Gln His Val His Lys Asp Ala
225                 230                 235                 240

Ser Leu Asn Pro Ala Gly Phe Ile Pro Ala Asn Thr Asp Phe Tyr Lys
                245                 250                 255

Tyr Ser Gly Ser Leu Thr Thr Pro Pro Cys Ser Glu Gly Val Tyr Trp
                260                 265                 270

Met Val Phe Lys Gln Pro Ile Gln Ala Ser Ala Glu Gln Ile Gln Gln
                275                 280                 285

Leu Asn Glu Leu Met Gly Asp Asn Ser Arg Pro Phe Gln Ala Thr Asn
290                 295                 300

Ala Arg Ser Val Leu Lys Ser Trp Ala Asp Gln Leu Gln Glu Pro Pro
305                 310                 315                 320

Leu Tyr Glu Phe Tyr
                325

<210> SEQ ID NO 39
<211> LENGTH: 315
<212> TYPE: PRT
<213> ORGANISM: Sulfurivirga caldicuralii

<400> SEQUENCE: 39

Met Lys Lys Thr Leu Leu Ala Thr Leu Ile Ala Ala Met Thr Pro
1               5                   10                  15

Ala Ala Met Ala Glu Thr His His Gly His Ala Ile Lys Val Glu
                20                  25                  30

His Ala Lys Ala Pro Leu Ile Asn Leu Glu Glu Glu Ala Lys Lys Tyr
                35                  40                  45

Ala Gly Val Asp Thr His Ala Ala Asp His Ala Lys Lys Ser Asp
            50                  55                  60

His Ala Asp Asp Lys Lys His Ala Ala His Lys Ala His Trp Gly Tyr
65                  70                  75                  80

Ser Gly Glu Thr Gly Pro Asp His Trp Gly Asp Leu Asp Pro Lys Tyr
                85                  90                  95

Ile Met Cys Lys Leu Gly Val Asn Gln Ser Pro Ile Asp Ile Arg Asp
                100                 105                 110

Lys Val Ala Val Gly Thr Val Gly Leu Pro Gly Leu Thr Val Ala Tyr
            115                 120                 125

Gly Gln Pro Gln Leu Arg Val Ile Asn Asn Gly His Thr Ile Gln Val
130                 135                 140

Asn Tyr Pro Ile Gly Asn Ser His Ile Thr Val Gly Asn His Arg Phe
145                 150                 155                 160

Glu Leu Leu Gln Phe His Phe His Thr Pro Ser Glu His Thr Lys Glu
                165                 170                 175

Gly Phe Asn Tyr Pro Met Glu Met His Leu Val His Lys Asp Gly Asp
                180                 185                 190

Gly Asn Leu Ala Val Ile Gly Ile Leu Tyr Lys Glu Gly Glu His Asn
            195                 200                 205

Ala Glu Leu Gln Lys Leu Ile Asp His Leu Pro Lys Asp Val Gly Lys
        210                 215                 220

Glu His His Tyr Lys Gly Val His Ile Asp Leu Thr Lys Phe Phe Pro
225                 230                 235                 240

Ala Gln Lys Leu Phe Tyr Lys Tyr Ser Gly Ser Leu Thr Thr Pro Pro
                245                 250                 255
```

```
Cys Ser Glu Gly Val Tyr Trp Met Val Phe Lys Gln Pro Ile Glu Ala
                260                 265                 270

Ser Ala Asp Gln Ile Asp Ala Met His Ala Leu Leu His Thr Asn Asn
            275                 280                 285

Arg Pro Val Gln Gly Val His Ser Arg His Val Leu Lys Ser Trp Ala
        290                 295                 300

Glu Pro Asp Met Ser Asn Asp Phe Tyr Tyr Tyr
305                 310                 315

<210> SEQ ID NO 40
<211> LENGTH: 333
<212> TYPE: PRT
<213> ORGANISM: Thiomicrospira pelophila

<400> SEQUENCE: 40

Met Lys Lys Trp Leu Ala Ala Trp Ala Phe Ser Leu Ser Thr Gly
1               5                   10                  15

Val Trp Ala Glu Glu Pro Leu Ile Asp Leu Ala Ser Glu Val Gln Pro
            20                  25                  30

Ala Val Ala Glu Gln Gly Gln Val Gln Thr Gln Ser Glu Pro Asp Pro
        35                  40                  45

Glu Ser Lys Ser Ser Glu Ser Thr Glu Pro Ala Ala Ser Asn Thr Asp
    50                  55                  60

Gly Ala Thr Asn Lys Ser Asp Thr Lys Pro Asp Lys Pro Ser Leu Pro
65                  70                  75                  80

Pro Val Ala Glu Pro Ala Glu Trp Gly Tyr Val Ala Glu Gln Ala
                85                  90                  95

Pro Arg Tyr Trp Ala Gln Leu Asp Ser Arg Tyr Gln Thr Cys Ala Leu
            100                 105                 110

Gly Lys Asn Gln Ser Pro Ile Asn Leu Thr Ser Gln Ala Val Gln
        115                 120                 125

Thr Arg Gly Leu Pro Ala Leu Asp Ile Ala Tyr Arg Asp Val Pro Leu
    130                 135                 140

Arg Leu Ile His Ser Asp His Gly Leu Arg Gly Asn Tyr Pro Leu Gly
145                 150                 155                 160

Ser Tyr Ile Gln Leu Gly Lys Gln Arg Tyr Glu Leu Thr His Tyr Thr
                165                 170                 175

Phe His Thr Pro Ser Glu His His Ile Glu Gly Phe Ala Tyr Pro Met
            180                 185                 190

Glu Ile Gln Leu Met His Arg Asn Gly Glu Gly Asn Gln Val Val Met
        195                 200                 205

Ser Val Ile Val Gln Glu Gly Glu Asn Asn Glu Gln Leu Ala Thr Ile
    210                 215                 220

Leu Lys Asn Leu Pro Asn Lys Lys Asp Lys Leu Gln Val Phe Glu Lys
225                 230                 235                 240

Val Asn Phe Asn Pro Val Lys Phe Leu Pro Gly Asp Lys Arg Phe Tyr
                245                 250                 255

Arg Tyr Ile Gly Ser Met Thr Gln Pro Pro Cys Glu Glu Gly Val Val
            260                 265                 270

Trp Leu Val Phe Ser Lys Pro Ile Gln Ala Ser Ile Ser Gln Leu Val
        275                 280                 285

Lys Leu Asn Glu Leu Met Gly Asp Asn Ala Arg Pro Leu Gln Gly Leu
    290                 295                 300

Asn Gly Arg Val Pro Met Lys Ser Trp Met Gln Glu Ser Ala Asp Ser
```

```
                    305                 310                 315                 320

His Pro Ala Gln Ser Ser Pro Gly Tyr Tyr Phe Asp Tyr
                325                 330

<210> SEQ ID NO 41
<211> LENGTH: 352
<212> TYPE: PRT
<213> ORGANISM: Thiomicrospira microaerophila

<400> SEQUENCE: 41

Met Ala Phe Asp Gly Asp Ala Ser Val Lys Gly Val Ser Met Gly Cys
1               5                   10                  15

Arg Gln Leu Arg Trp Phe Phe Leu Leu Met Ser Met Thr Trp Leu Val
                20                  25                  30

Ser Ala Asn Glu Pro Leu Leu Asp Leu Ala Ala Glu Leu Glu Ala His
            35                  40                  45

Met Ala Ala Gln Glu Arg Ala Gly Gln Thr Pro Asp Ala Ser Asp Ala
        50                  55                  60

Pro Val Ala Glu Glu Ala Ala Pro Ser Ala Glu Arg Gln Gly Ala Pro
65                  70                  75                  80

Ala Glu Ala Asp Ala Glu Leu Lys Ala Ser Ser Gly Glu Arg Val Pro
                85                  90                  95

Pro Val Thr Pro Glu Pro Ala Lys Trp Gly Tyr Ser Ala Asp Lys Ala
            100                 105                 110

Pro Arg Phe Trp His Arg Leu Asp Pro Asn Tyr Leu Gly Cys Ala Thr
        115                 120                 125

Gly Val Ile Gln Ser Pro Ile Asn Leu Ser Ser His Gln Ala Ile Asn
130                 135                 140

Ala Pro Ser Met Pro Gly Leu Asp Ile Ile Tyr Arg Pro Val Pro Leu
145                 150                 155                 160

Arg Leu Thr His Asp His Gln Gly Leu Arg Gly Asp Tyr Pro Leu Gly
                165                 170                 175

Ser Phe Met Arg Leu Asp Asn Gln Arg Phe Glu Phe Thr His Tyr Arg
            180                 185                 190

Phe Arg Thr Pro Ser Glu His His Leu Glu Gly Phe Ala Tyr Pro Met
        195                 200                 205

Glu Ile Gln Phe Phe His Arg Asp Gly Glu Gly Arg Gln Leu Val Met
210                 215                 220

Ser Val Leu Val Gln Glu Gly Arg Pro Asn Val Ser Leu Ala Thr Ile
225                 230                 235                 240

Leu Glu His Leu Pro Lys Glu Lys Asp Ser Leu His Leu Val Glu Asp
                245                 250                 255

Leu Asn Phe Asn Pro Val Arg Phe Leu Pro Glu Ser Lys His Phe Tyr
            260                 265                 270

Arg Tyr Leu Gly Ser Leu Thr Thr Pro Pro Cys Thr Glu Gly Val Ile
        275                 280                 285

Trp Ile Val Phe Gln Gln Pro Ile Glu Ala Ser Ile Arg Gln Leu Ile
290                 295                 300

Thr Leu His Gln Val Leu Gly Asp Asn Ser Arg Pro Val Gln Ala Leu
305                 310                 315                 320

Asn Gly Arg Leu Pro Leu Lys Ser Trp Leu Arg Asp Ala Ser Arg Ser
                325                 330                 335

Gly Gly Gln Phe Ser Ala Pro Thr Thr Pro Gly Tyr Tyr Phe Asp Phe
            340                 345                 350
```